US008071021B2

(12) United States Patent
Hill

(10) Patent No.: US 8,071,021 B2
(45) Date of Patent: Dec. 6, 2011

(54) HYDROGEN PEROXIDE VAPORIZER

(75) Inventor: Aaron L. Hill, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 686 days.

(21) Appl. No.: 11/741,299

(22) Filed: Apr. 27, 2007

(65) Prior Publication Data
US 2007/0253859 A1 Nov. 1, 2007

Related U.S. Application Data

(60) Provisional application No. 60/796,427, filed on May 1, 2006.

(51) Int. Cl.
*A61L 2/20* (2006.01)
(52) U.S. Cl. ............. 422/28; 422/30; 422/302; 422/305
(58) Field of Classification Search .................. None
See application file for complete search history.

(56) References Cited

U.S. PATENT DOCUMENTS

| 4,642,165 | A | * | 2/1987 | Bier ................................ 422/28 |
| 4,742,667 | A | | 5/1988 | Muller et al. .................... 53/167 |
| 4,843,867 | A | | 7/1989 | Cummings ........................ 73/23 |
| 4,952,370 | A | | 8/1990 | Cummings et al. .............. 422/28 |
| 4,956,145 | A | | 9/1990 | Cummings et al. .............. 422/28 |
| 5,122,344 | A | | 6/1992 | Schmoegner ................. 422/111 |
| 5,173,258 | A | | 12/1992 | Childers ........................ 422/27 |
| 5,258,162 | A | | 11/1993 | Andersson et al. ............. 422/28 |
| 5,492,672 | A | | 2/1996 | Childers et al. ................. 422/28 |
| 5,508,009 | A | | 4/1996 | Rickloff et al. ............... 422/292 |
| 5,667,753 | A | | 9/1997 | Jacobs et al. .................... 422/29 |
| 5,876,664 | A | | 3/1999 | Childers et al. ................. 422/28 |
| 5,906,794 | A | | 5/1999 | Childers ........................ 422/28 |
| 6,077,480 | A | | 6/2000 | Edwards et al. ............... 422/28 |

(Continued)

FOREIGN PATENT DOCUMENTS

JP 2001-183326 7/2001
(Continued)

OTHER PUBLICATIONS

U.S. Appl. No. 11/421,265, filed May 31, 2006, Buczynski, entitled: Decontamination System With Air Bypass.

(Continued)

*Primary Examiner* — Walter Griffin
*Assistant Examiner* — Timothy Cleveland
(74) *Attorney, Agent, or Firm* — Kusner & Jaffe; Michael A. Centanni

(57) ABSTRACT

A method of decontaminating articles, comprising the steps of:
 (a) moving a plurality of articles having a known temperature along a first path;
 (b) conveying a carrier gas along a second path that includes an elongated plenum, the second path intersecting the first path downstream from the plenum;
 (c) heating the carrier gas to a temperature of at least about 105° C. at a location upstream of the plenum;
 (d) introducing into the carrier gas in the plenum an atomized mist of a liquid hydrogen peroxide of known concentration; and
 (e) controlling the following:
  (1) the volumetric flow of carrier gas along the second path;
  (2) the volume of hydrogen peroxide introduced into the carrier gas; and
  (3) the temperature of the carrier gas introduced into the plenum, such that the concentration of the vaporized hydrogen peroxide in the carrier gas where the first path intersects the second path has a dew point temperature below the known temperature of the articles.

25 Claims, 11 Drawing Sheets

U.S. PATENT DOCUMENTS

| | | | |
|---|---|---|---|
| 6,096,265 A * | 8/2000 | Mezger et al. | 422/28 |
| 6,120,730 A | 9/2000 | Palaniappan et al. | 422/28 |
| 6,475,435 B1 | 11/2002 | Taggart | 422/33 |
| 6,936,434 B2 | 8/2005 | McDonnell et al. | 435/31 |
| 6,953,549 B2 | 10/2005 | Hill et al. | 422/30 |
| 7,157,046 B2 | 1/2007 | McVey et al. | 422/28 |
| 7,186,374 B2 | 3/2007 | Zelina et al. | 422/28 |
| 7,238,330 B2 | 7/2007 | Hill et al. | 422/292 |
| 2002/0114727 A1 | 8/2002 | McVey et al. | 422/4 |
| 2002/0159915 A1 | 10/2002 | Zelina et al. | 422/3 |
| 2004/0182855 A1 | 9/2004 | Centanni | 219/628 |
| 2005/0252274 A1 | 11/2005 | Centanni | 73/23.2 |
| 2006/0008383 A1 | 1/2006 | Moller et al. | 422/62 |
| 2006/0088441 A1 | 4/2006 | Hill | 422/30 |
| 2007/0098592 A1 | 5/2007 | Buczynski et al. | 422/3 |

FOREIGN PATENT DOCUMENTS

| | | |
|---|---|---|
| JP | 2003-339829 | 12/2003 |
| WO | WO 00/038746 | 7/2000 |
| WO | WO 2006/057523 | 6/2006 |

OTHER PUBLICATIONS

U.S. Appl. No. 11/463,608, filed Aug. 10, 2006, Hill, entitled: Modular Decontamination System.

U.S. Appl. No. 11/740,973, filed Apr. 27, 2007, Hill, entitled: Vaporized Hydrogen Peroxide Probe Calibration Rig.

U.S. Appl. No. 11/741,069, filed Apr. 27, 2007, Hill, entitled: Vaporized Hydrogen Peroxide Decontamination System With Concentration Adjustment Mode.

U.S. Appl. No. 11/838,327, filed Aug. 14, 2007, Hill, entitled: Method and Apparatus for Decontaminating a Region Without Dehumidification.

* cited by examiner

HYDROGEN PEROXIDE VAPORIZER

This application claims the benefit of U.S. Provisional Application No. 60/796,427, filed on May 1, 2006.

FIELD OF THE INVENTION

The present invention relates to the generation of vaporized hydrogen peroxide, and more particularly, to a system for generating large amounts of vaporized hydrogen peroxide and a method of operating the same.

BACKGROUND OF THE INVENTION

It is known to use hydrogen peroxide ($H_2O_2$) in sterilization and other processes. In a sterilization process, liquid hydrogen peroxide is vaporized to form vaporized hydrogen peroxide (VHP). The vaporized hydrogen peroxide is typically produced from a liquid mixture of hydrogen peroxide and water. Care must be taken when vaporizing this mixture due to the difference in the boiling points between water and hydrogen peroxide. In this respect, water boils at 100° C., whereas pure hydrogen peroxide boils at 150° C. Accordingly, when a mixture of water and hydrogen peroxide is vaporized, the water tends to boil before the hydrogen peroxide unless the mixture is flash vaporized. In conventional systems, flash vaporization is accomplished by dripping a small amount of the water and the hydrogen peroxide mixture on a hot surface. Air is directed over the hot surface to conduct away the vaporized hydrogen peroxide.

U.S. Pat. No. 2,491,732 discloses a conventional vaporized hydrogen peroxide (VHP) vaporizer. A problem with the aforementioned drip method of vaporization is that a hot surface must be maintained to vaporize the liquid hydrogen peroxide and water mixture. Testing has shown that an injection rate of up to 5 grams per minute per injection port can be achieved with current drip-method vaporizers. At higher injection rates, individual droplets can no longer be maintained. In other words, the drip-type vaporizer is limited in the amount of vaporized hydrogen peroxide it can produce within given size limits. This limitation prevents drip-type vaporizers from being used in certain high volume sterilizing processes where it is necessary to sterilize large numbers of articles and devices in a short period of time.

Another problem with vaporized hydrogen peroxide decontamination systems is preventing condensation of the vaporized hydrogen peroxide on the articles or surfaces to be decontaminated.

It is therefore desirable to have a high-capacity vaporized hydrogen peroxide generator capable of generating high volumes of vaporized hydrogen peroxide at concentration levels that will not condensate on the articles or surfaces to be decontaminated.

The present invention provides a hydrogen peroxide vaporizer capable of generating large volumes of vaporized hydrogen peroxide at concentration levels that will not condensate on the articles or surfaces to be decontaminated.

SUMMARY OF THE INVENTION

In accordance with a preferred embodiment of the present invention, there is provided a method of decontaminating articles, comprising the steps of:

(a) moving a plurality of articles having a known temperature along a first path;

(b) conveying a carrier gas along a second path that includes an elongated plenum, the second path intersecting the first path downstream from the plenum;

(c) heating the carrier gas to a temperature of at least about 105° C. at a location upstream of the plenum;

(d) introducing into the carrier gas in the plenum an atomized mist of a liquid hydrogen peroxide of known concentration; and (e) controlling the following:
 (1) the volumetric flow of carrier gas along the second path;
 (2) the volume of hydrogen peroxide introduced into the carrier gas; and
 (3) the temperature of the carrier gas introduced into the plenum, such that the concentration of the vaporized hydrogen peroxide in the carrier gas where the first path intersects the second path has a dew point temperature below the known temperature of the articles.

In accordance with another aspect of the present invention, there is provided a method of decontaminating articles, comprising the steps of:

(a) moving a plurality of articles along a first path that includes a decontamination chamber;

(b) conveying a carrier gas along a second path that includes an elongated plenum and the decontamination chamber, the decontamination chamber being downstream from the elongated plenum;

(c) heating the carrier gas at a location upstream of the plenum to a temperature sufficient to vaporize hydrogen peroxide;

(d) introducing liquid hydrogen peroxide of a known concentration into the carrier gas in the plenum to produce vaporized hydrogen peroxide in the plenum; and (e) exposing the articles in the decontamination chamber to the vaporized hydrogen peroxide at an temperature above a pre-selected dew point temperature by controlling the following:
 (1) the volumetric flow of carrier gas moving along the second path;
 (2) a rate of introduction of the liquid hydrogen peroxide introduced into the carrier gas; and
 (3) the temperature of the carrier gas introduced into the plenum.

In accordance with still another aspect of the present invention, there is provided a method of decontaminating articles, comprising the steps of:

(a) moving a plurality of articles along a first path through a decontamination chamber, the articles having a predetermined temperature;

(b) conveying a carrier gas along a second path that includes an elongated plenum and the decontamination chamber, the decontamination chamber being downstream from the elongated plenum;

(c) heating the carrier gas at a location upstream of the plenum to a temperature sufficient to vaporize hydrogen peroxide;

(d) introducing liquid hydrogen peroxide of a known concentration into the carrier gas in the plenum to produce vaporized hydrogen peroxide in the plenum;

(e) measuring a temperature and a pressure of the carrier gas at discrete locations along the second path;

(f) determining a dew point temperature of the vaporized hydrogen peroxide and the water vapor in the carrier gas based upon the temperature and the pressure of the carrier gas in the second path;

(g) introducing the vaporized hydrogen peroxide into the decontamination chamber; and (h) controlling the dew point temperature of the vaporized hydrogen peroxide to be at or below a pre-selected dew point temperature by controlling the following:
(1) the volumetric flow of carrier gas moving along the second path;
(2) a rate of introduction of the liquid hydrogen peroxide introduced into the carrier gas; and
(3) the temperature of the carrier gas introduced into the plenum.

In accordance with yet another aspect of the present invention, there is provided a method of decontaminating articles, comprising the steps of:
(a) moving a plurality of articles along a first path that includes a decontamination chamber, the articles having a predetermined temperature;
(b) conveying a carrier gas along a second path that includes an elongated plenum and the decontamination chamber, the decontamination chamber disposed downstream of the elongated plenum;
(c) heating the carrier gas at a location upstream of the plenum to a temperature sufficient to vaporize hydrogen peroxide;
(d) introducing liquid hydrogen peroxide of a known concentration into the carrier gas in the plenum at a fixed rate to produce vaporized hydrogen peroxide in the plenum;
(e) exposing the articles in the decontamination chamber to the vaporized hydrogen peroxide; and
(f) maintaining the vaporized hydrogen peroxide at or below a pre-selected temperature by controlling the following:
(1) the volumetric flow of carrier gas moving along the second path; and
(2) the temperature of the carrier gas introduced into the plenum.

In accordance with still another aspect of the present invention, there is provided a method of decontaminating articles, comprising the steps of:
(a) moving a plurality of articles along a first path that includes a decontamination chamber;
(b) conveying a carrier gas along a second path that includes an elongated plenum and the decontamination chamber, the decontamination chamber disposed downstream of the elongated plenum;
(c) heating the carrier gas at a location upstream of the plenum to a temperature sufficient to vaporize hydrogen peroxide;
(d) introducing liquid hydrogen peroxide of a known concentration into the carrier gas in the plenum to produce vaporized hydrogen peroxide in the plenum;
(e) exposing the articles in the decontamination chamber to the vaporized hydrogen peroxide; and
(f) maintaining the vaporized hydrogen peroxide at a temperature at or below a pre-selected temperature and the vaporized hydrogen peroxide at a concentration at or below a pre-selected concentration by controlling the following:
(1) the volumetric flow of carrier gas moving along the second path; and
(2) a rate of introduction of the liquid hydrogen peroxide into the carrier gas; and
(3) the temperature of the carrier gas introduced into the plenum.

In accordance with still another aspect of the present invention, there is provided an apparatus for decontaminating articles comprised of a decontamination chamber. A conveyor conveys articles to be decontaminated along a first path through the decontamination chamber. A vaporizing unit connects to the decontamination chamber. The vaporizing unit is disposed above the decontamination chamber. A blower conveys a carrier gas through the vaporizing unit and through the decontamination chamber. A heating means heats the carrier gas flowing through the vaporizing unit. A source of liquid hydrogen peroxide fluidly connects to the vaporizing unit. An injection device injects liquid hydrogen peroxide into the vaporizing unit.

In accordance with still another aspect of the present invention, there is provided an apparatus for decontaminating articles in a decontamination chamber having a reservoir assembly comprised of a first storage tank connected to a source of hydrogen peroxide, and a second storage tank connects to a source of hydrogen peroxide. A collection tank is connected to the first storage tank and the second storage tank to receive hydrogen peroxide therefrom. The collection tank also connects to a vaporizing unit. A valve means selectively fluidly communicates the first storage tank and the second storage tank with the collection tank. The valve means also selectively fluidly communicates the first storage tank and the second storage tank with the source of liquid hydrogen peroxide. A vent line has one end connected to the collection tank. A second end of the vent line is disposed at a location above a top of the first storage tank and the second storage tank. A vent valve is disposed in the vent line to control flow therethrough.

An advantage of the present invention is a high-capacity vaporized hydrogen peroxide (VHP) generator.

Another advantage of the present invention is a decontamination system capable of producing large quantities of vaporized hydrogen peroxide.

Another advantage of the present invention is a decontamination system as described above having several methods for confirming the flow of vaporized hydrogen peroxide through the system.

Another advantage of the present invention is a decontamination system as described above that is capable of modifying the flow of carrier gas therethrough.

Another advantage of the present invention is a decontamination system as described above that is capable of modifying the injection rate of liquid sterilant into the system.

Another advantage of the present invention is a decontamination system as described above that is capable of modifying the temperature of a carrier gas flowing therethrough.

Another advantage of the present invention is a decontamination system as described above that operates to maintain the concentration of vaporized hydrogen peroxide in a carrier gas at a level wherein the vaporized hydrogen peroxide has a dew point below the initial temperature of articles to be decontaminated.

A still further advantage of the present invention is a decontamination system as described above wherein system components are arranged such that un-vaporized hydrogen peroxide (if present) will flow downward through a system to be collected at a low point in the system.

Another advantage of the present invention is a decontamination system as described above having a sterilant supply system with a settling tank to eliminate entrained or trapped gas in a sterilant supply line to a vaporizer.

Another advantage of the present invention is a decontamination system as described above having an air process unit for filtering and drying air used within the system.

Another advantage of the present invention is a method of operating a system as described above to prevent condensation on articles or surfaces to be decontaminated.

Another advantage of the present invention is a method of operating a system as described above to maintain a desired concentration of vaporized hydrogen peroxide at the location where articles or surfaces are to be decontaminated.

Another advantage of the present invention is a method of operating a system as described above to maintain a fixed injection rate of liquid sterilant.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
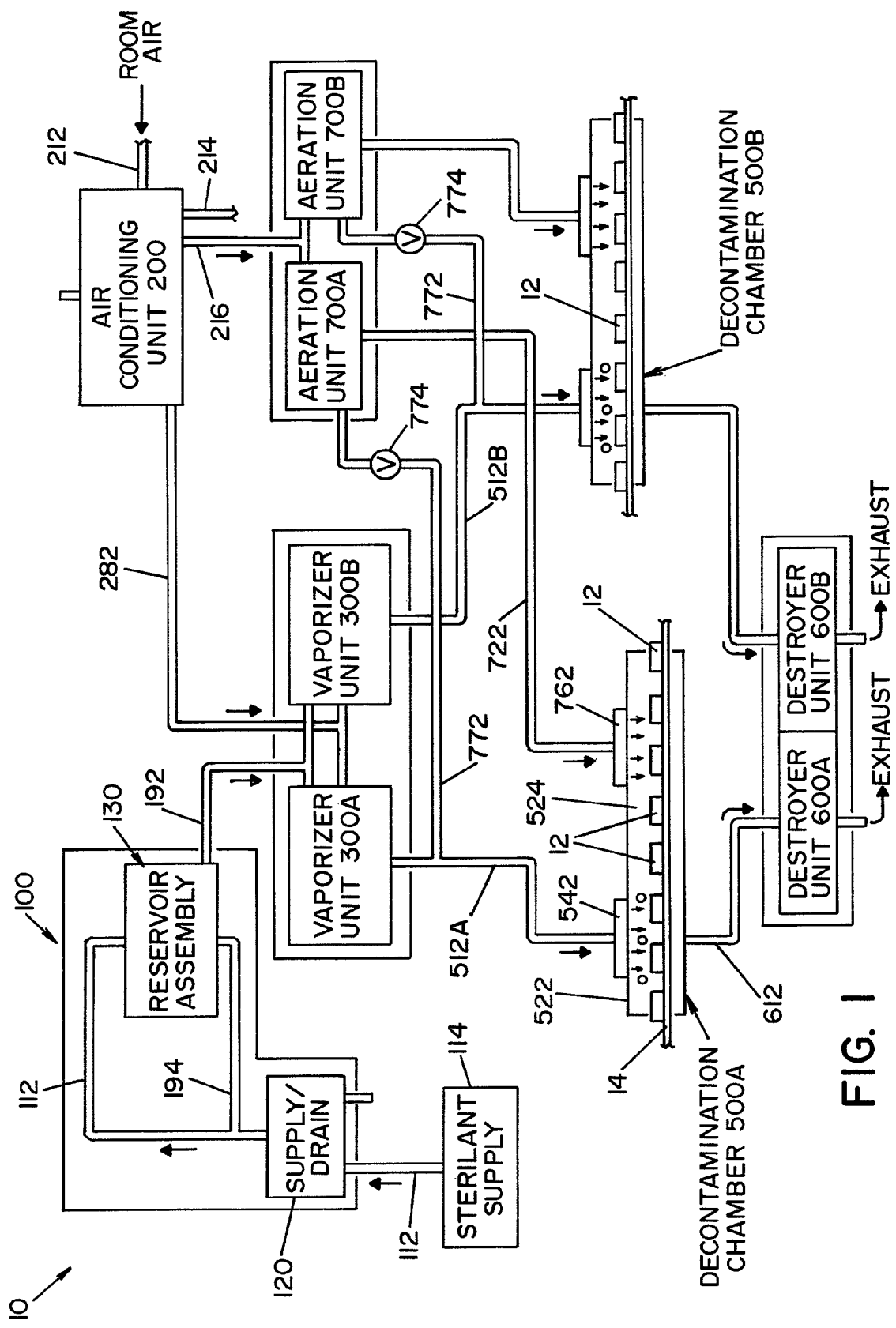
FIG. 1 is a drawing schematically illustrating a high-capacity vaporized hydrogen peroxide decontamination system, illustrating a preferred embodiment of the present invention.

Referring now to the drawings wherein the showings are for the purpose of illustrating a preferred embodiment of the invention only, and not for the purpose of limiting same, FIG. 1 shows a vaporized hydrogen peroxide decontamination system 10 for continuously decontaminating articles 12 moving along a conveyor belt 14, illustrating a preferred embodiment of the present invention.

Broadly stated, a decontamination system 10, according to the present invention, is comprised of a sterilant supply unit, an air conditioning unit, a vaporizer unit, a decontamination room or isolator, a destroyer unit and an aeration unit. In the embodiment shown, decontamination system 10 includes a single sterilant supply unit 100, a single air conditioning unit 200, two vaporizer units 300A, 300B, two decontamination rooms 500A, 500B, two destroyer units 600A, 600B and two aeration units 700A, 700B.

Sterilant Supply Unit 100

Figure 2:
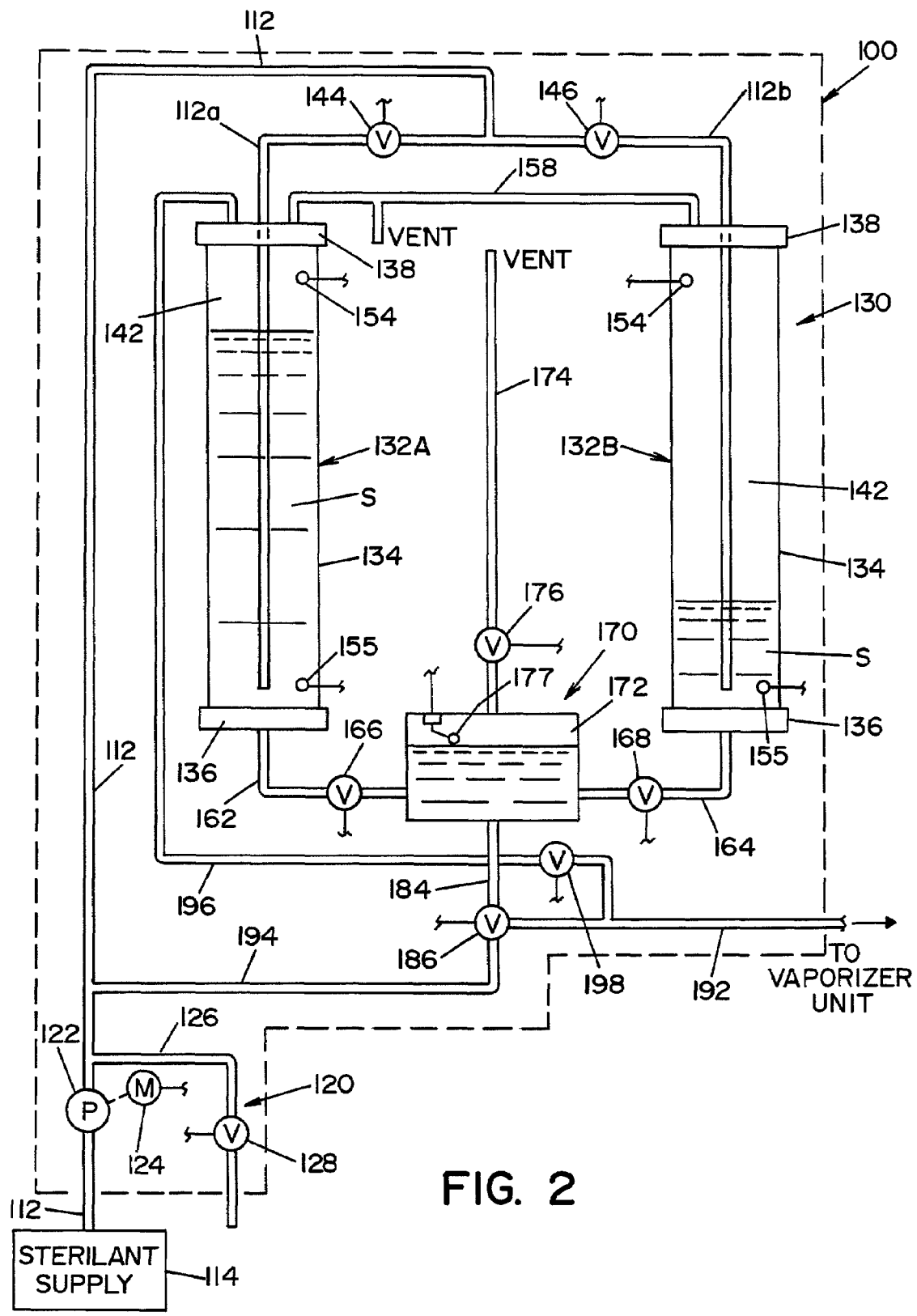
FIG. 2 is a drawing schematically illustrating a sterilant supply unit from the decontamination system shown in FIG. 1.

Referring now to FIG. 2, sterilant supply unit 100 is best seen. A supply line 112 connects sterilant supply unit 100 to an external supply 114 of liquid sterilant. A pump and drain assembly 120 is connected to supply line 112. Pump and drain assembly 120 includes a pump 122 driven by a motor 124. Pump 122 and motor 124 are designed to convey metered amounts of liquid sterilant to a reservoir assembly 130.

Reservoir assembly 130 preferably includes two reservoir tanks 132A, 132B. Two sterilant holding tanks 132A, 132B are provided to allow continuous, uninterrupted flow of sterilant to vaporizer units 300A, 300B. In this respect, one holding tank 132A may be filled with sterilant, while the other tank 132B is being used to provide sterilant to vaporizer units 300A, 300B, as shall be described in greater detail below. Tanks 132A, 132B are essentially identical, and therefore, only tank 132A shall be described in detail. It being understood that the description of tank 132A applies to tank 132B.

Tank 132A is generally columnar in shape, and is comprised of a tubular shell or wall 134 having a base 136 and a cover 138 at the ends thereof. In a preferred embodiment, tubular shell 134 is cylindrical in shape and is formed of a translucent material. Tank 132A defines an inner chamber 142 for holding a liquid sterilant S. Supply line 112 is connected to reservoir tanks 132A, 132B by branch supply lines 112a, 112b. Valves 144, 146 are disposed respectively in branch supply lines 112a, 112b to control flow of liquid sterilant S to reservoir tanks 132A, 132B. Each tank 132A, 132B includes level sensor 154. Sensor 154 is provided to indicate an "overfill level," as shall be described in greater detail below. A pressure sensor 155 is provided at the bottom of each tank 132A, 132B to provide pressure signals that are indicative of the level of fluid in each tank 132A, 132B.

Tanks 132A, 132B are connected at their bottom ends to a holding tank 170 by fluid conduits 162, 164, respectively. Control valves 166, 168 are disposed respectively in fluid conduits 162, 164 to control the flow of sterilant from reservoir tanks 132A, 132B to holding tank 170. The upper ends of reservoir tanks 132A, 132B are connected to a vent line 158, as schematically illustrated in FIG. 2.

Holding tank 170 defines air enclosed holding chamber 172. A vent line 174 extends upwardly from holding chamber 172. A control valve 176 is disposed within vent line 174 to control flow therethrough. As best seen in FIG. 2, vent line 174 has a length such that the upper end of vent line 174 is disposed at the upper ends of reservoir tanks 132A, 132B. A level sensor 177 is disposed within holding chamber 172 of holding tank 170 at a predetermined level. A level sensor 177 is disposed within holding tank 170. In the embodiment shown, level sensor 177 is a float switch.

A fluid conduit 184 extending from the bottom of holding tank 170 connects holding chamber 172 to a control valve 186 that regulates flow of sterilant from holding tank 170 to either a vaporizer feed line 192 or to a drain line 194 that is connected to supply line 112. As illustrated in FIG. 2, drain line 194 is in fluid communication with drain line 126 of pump and drain assembly 120. A return line 196 extends from vaporizer feed line 192 to the top of tank 132A. A control valve 198 is disposed within return line 196 to control the flow of sterilant therethrough.

Vaporizer feed line 192 is connected to vaporizer unit 300A and vaporizer unit 300B, as illustrated in the drawings. Sterilant from holding tank 170 is preferably fed by gravity to vaporizer units 300A, 300B. Accordingly, in the embodiment shown, holding tank 170 and reservoir tanks 132A, 132B are disposed above vaporizer units 300A, 300B, i.e., at a higher elevation.

Air Conditioning Unit 200

Figure 5:
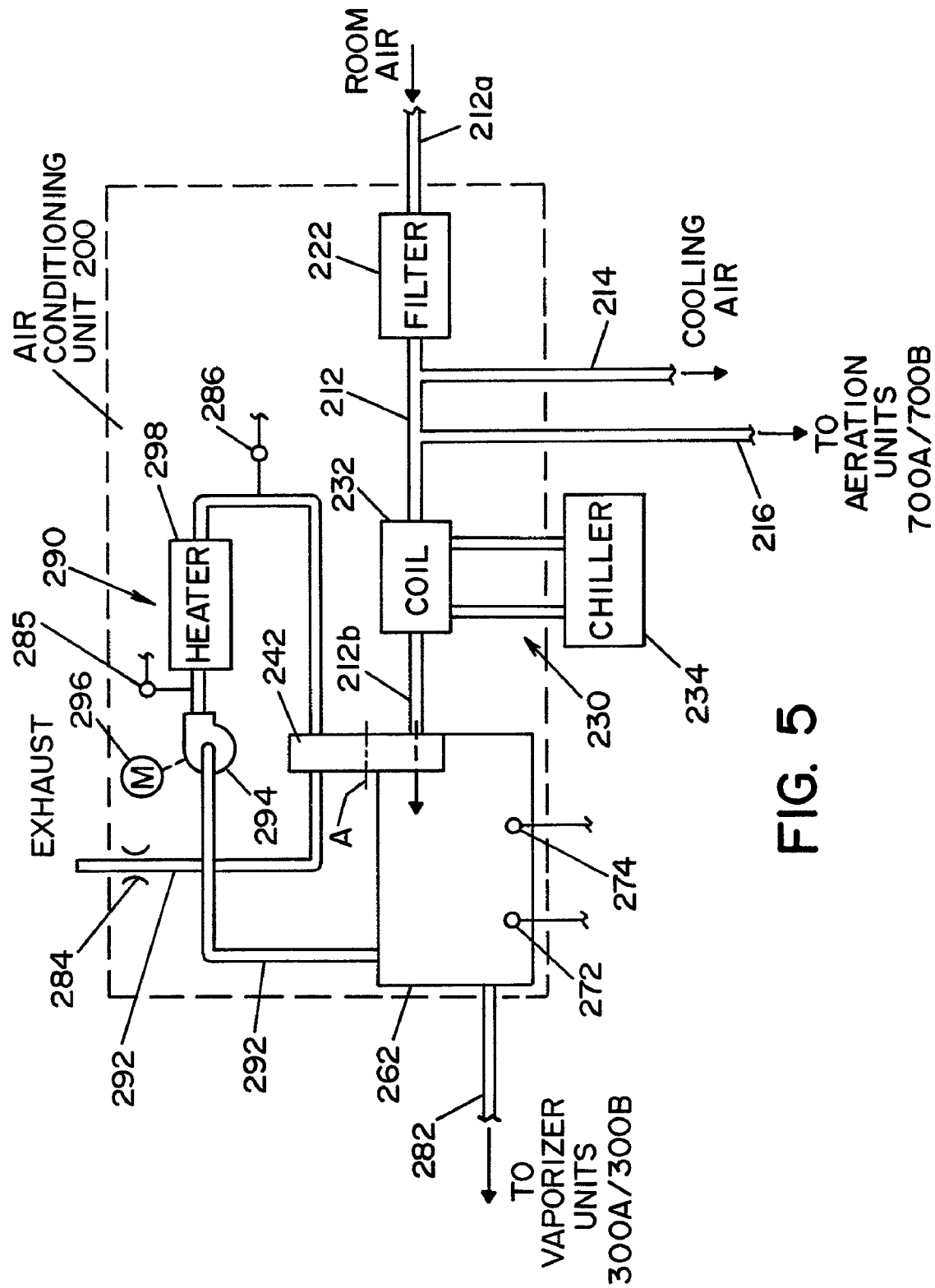
FIG. 5 is a drawing schematically illustrating an air conditioning unit from the decontamination system shown in FIG. 1.

Referring now to FIG. 5, the air conditioning unit 200 is best illustrated. Air conditioning unit 200 is provided to condition, i.e., to filter and to dry air used in vaporizer units 300A, 300B, and to filter air used by aeration units 700A, 700B. Air conditioning unit 200 is basically comprised of a filter 222, a cooling assembly 230 and a desiccant wheel 242 arranged in series.

An air inlet conduit 212 has a first end 212a that communicates with the environment, namely room air. Another end 212b of air inlet conduit 212 is connected to chamber 262 within air conditioning unit 200. Filter 222 is disposed within air inlet conduit 212 to filter air flowing therethrough. Filter 222 is preferably a HEPA filter. Cooling assembly 230 is disposed downstream from filter 222. Cooling assembly 230 is comprised of a cooling coil 232 and a chiller 234 that is connected to cooling coil 232. Cooling coil 232 surrounds air inlet conduit 212. Chiller 234 is dimensioned to provide sufficient cooling to coil 232 surrounding air inlet conduit 212 such that air flowing through air inlet conduit 212 is chilled to precipitate moisture within the air. In other words, chiller 234 has sufficient capacity to dehumidify air flowing through air inlet conduit 212. Between filter 222 and cooling coil 232, an air supply line 214 is connected to air inlet conduit 212. Air supply line 214 provides filtered air throughout system 10 to cool electronics (not shown). A second air supply line 216 is connected to air inlet conduit 212 between filter 222 and cooling coil 232. Second air supply line 216 provides filtered air to aeration units 700A, 700B, as shall be described in greater detail below. Desiccant wheel 242, rotatable about a first axis "A," is disposed at end 212b of air inlet conduit 212, i.e., downstream from filter 222 and cooling coil 232. Desiccant wheel 242 is disposed such that half of wheel 242 rotates into chamber 262. End 212b of air inlet conduit 212 directs air flow through that portion of desiccant wheel 242 that is positioned within chamber 262. Desiccant material within desiccant wheel 242 is operable to absorb moisture in the air flowing through air inlet conduit 212. Thus, air entering chamber 262 has been filtered and dried by means of filter 222, cooling coil 232 and desiccant wheel 242. A humidity sensor 272 and a temperature sensor 274 are disposed within chamber 262 to monitor respectively the humidity and temperature of the air within chamber 262. Chamber 262 is in fluid communication with vaporizer units 300A, 300B via air line 282, as illustrated in FIG. 5.

Air conditioning unit 200 includes a regeneration system 290 for regenerating, i.e., removing moisture from, desiccant wheel 242. A regeneration conduit 292 is connected to chamber 262. A blower 294, driven by a motor 296, draws dried and filtered air within chamber 262 and directs the dried air through a heater 298 that heats the dry air. Regeneration conduit 292 is arranged to direct the heated, dried, filtered air through that portion of desiccant wheel 242 that is outside of chamber 262. As will be appreciated by those skilled in the art, the heated air dries, i.e., removes moisture from desiccant wheel 242. Moist air flowing from desiccant wheel 242 through regeneration conduit 292 flows out of air conditioning unit 200 through an orifice 284. A pressure transducer 285 is disposed at the outlet, i.e., downstream, of blower 294. Pressure transducer 285, in conjunction with orifice 284, is used to establish a desired air flow through conduit 292, to ensure proper moisture removal. A temperature sensor 286 monitors the temperature of the air exiting heater 298. The temperature in conduit 292 is controlled to ensure proper moisture removal.

Vaporizer Units 300A, 300B

Figure 3:
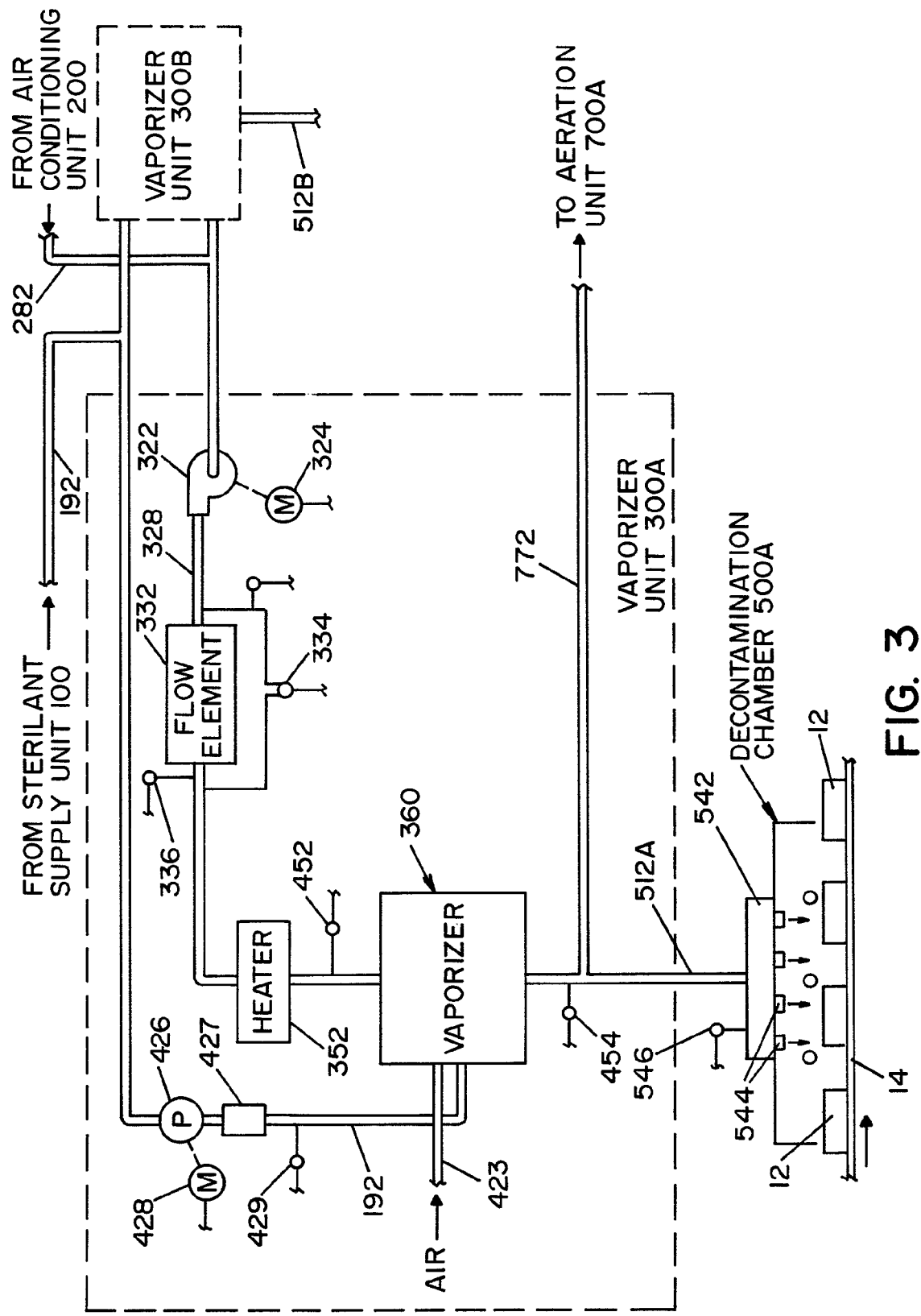
FIG. 3 is a drawing pictorially illustrating a vaporizer unit from the decontamination system shown in FIG. 1.

Referring now to FIGS. 3, 7, 8 and 9, vaporizer units 300A, 300B are best seen. Vaporizer units 300A, 300B are essentially identical, and therefore, only vaporizer unit 300A shall be described in great detail, it being understood that such description applies equally to vaporizer unit 300B. As illustrated in FIG. 3, vaporizer unit 300A (and vaporizer unit 300B) is connected to vaporizer feed line 192 from sterilant supply unit 100, and is connected to air line 282 from air conditioning unit 200.

Figure 7:
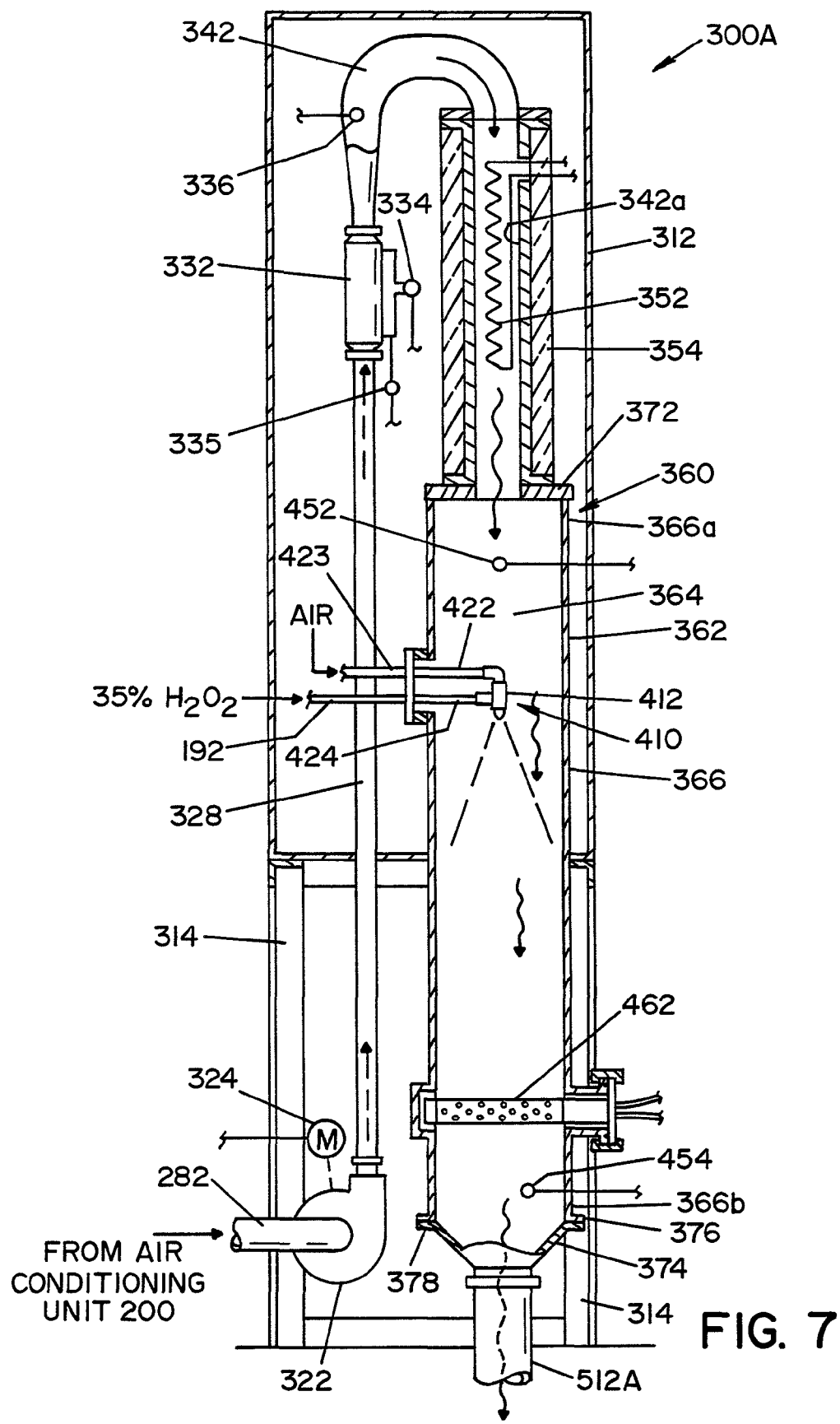
FIG. 7 is a sectional view of a vaporizer from the decontamination system shown in FIG. 1.

Vaporizer unit 300A is comprised of a blower 322, a flow element 332 for measuring airflow, a heater 352 and a vaporizer 360, that are all schematically illustrated in FIG. 3, and pictorially illustrated in FIG. 7.

In the embodiment shown, vaporizer unit 300A includes a cabinet or housing 312 mounted on a structural steel support frame 314. Cabinet 312 and support frame 314 together define an upright, columnar structure. A blower 322 is disposed at a bottom location of support frame 314. Blower 322 is driven by a motor 324. Motor 324 is preferably a variable speed motor, wherein the output of blower 322 can be controlled to increase air flow therethrough. The inlet of blower 322 is connected to air line 282 from air conditioning unit 200. When in operation, blower 322 draws air through air conditioning unit 200 where the air is then dried and filtered. In the embodiment shown, the outlet of blower 322 is connected to a vertical conduit 328. A flow element 332 is disposed within conduit 328 to measure air flow through conduit 328. Flow element 332 is preferably a Venturi device. A sensor 334 measures a pressure difference across the Venturi device and provides a signal indicative of the air flow through flow element 332. A Venturi device is preferable because of the high resolution of air flow it can provide and because of the low loss of power for the air flowing therethrough. A pressure sensor 335 is provided to measure the static pressure to flow element 332, to facilitate calculation of the mass air flow rate through conduit 328, as shall be described in greater detail below. A temperature sensor 336 is disposed downstream from flow element 332.

In the embodiment shown, a generally U-shaped conduit section 342 is connected to flow element 332 to redirect the flow of air. Conduit section 342 includes an elongated straight heater section 342a that is vertically oriented in the embodiment shown. As illustrated in FIG. 7, the passageway defined by conduit section 342 increases in a cross-sectional area from the end of conduit section 342, that connects to flow meter 332, to elongated straight heater section 342a. A heating element 352 is positioned within straight heater section 342a of conduit section 342 and is provided to heat the air flowing through conduit section 342. In the embodiment shown, heating element 352 is an electrical device. An insulating layer 354 surrounds and encloses heating element 352. Heating element 352 is designed to be capable of heating air flowing through conduit section 342 up to a temperature high enough to vaporize hydrogen peroxide and high enough to maintain a desired temperature sufficient to prevent condensation in decontamination system 10. In one embodiment, heating element 352 is capable of heating air flowing through conduit section 342 to at least about 105° C. In another embodiment, heating element 352 is capable of heating air flowing through conduit section 342 to at least 180° C. The increase in the cross-sectional area of conduit section 342 allows the smaller piping from flow element 332 to connect to the larger diameter of heater section 342a.

A vaporizer 360 is connected to the end of conduit section 342 downstream from heater 352. Vaporizer 360 is comprised of a housing 362 defining an elongated inner vaporizing plenum 364. In the embodiment shown, housing 362 is comprised of a rectangular shell 366 having a first end 366a having a flat cap 372 thereon, and a second end 366b having a funnel-shaped base 374. The cross-sectional area and the length of housing 362 are dimensioned to allow sufficient time for the liquid sterilant to be vaporized therein. First end 366a of vaporizer 360 defines an inlet end, and second end 366b of vaporizer 360 defines an outlet end. Shell 366, cap 372 and base 374 are preferably formed of metal, and more preferably, of aluminum. Cap 372 is secured to shell 366, preferably by welding. Conduit section 342 communicates with inner plenum 364 of vaporizer 360 through an opening in cap 372. Outlet end 366b of shell 366 includes an annular flange 376 for connecting to an annular flange 378 on base 374. Base 374 is funnel-shaped and connects vaporizer housing 362 to a vaporized hydrogen peroxide feed line 512A that in turn is connected to decontamination chamber 500A.

As illustrated in FIG. 7, vaporizer 360 is oriented such that the elongated vaporizer plenum 364 is vertically oriented. In this respect, heating element 352 and straight section 342a of conduit section 342 are vertically aligned with vaporizer plenum 364 so as to direct heated air downwardly through vaporizer plenum 364.

A sterilant injection system 410 is disposed within vaporizer plenum 364. Injection system 410 is centrally disposed within plenum 364, and is oriented to inject sterilant into plenum 364 in a downwardly direction toward second end 366b of vaporizer housing 362.

Figure 8:
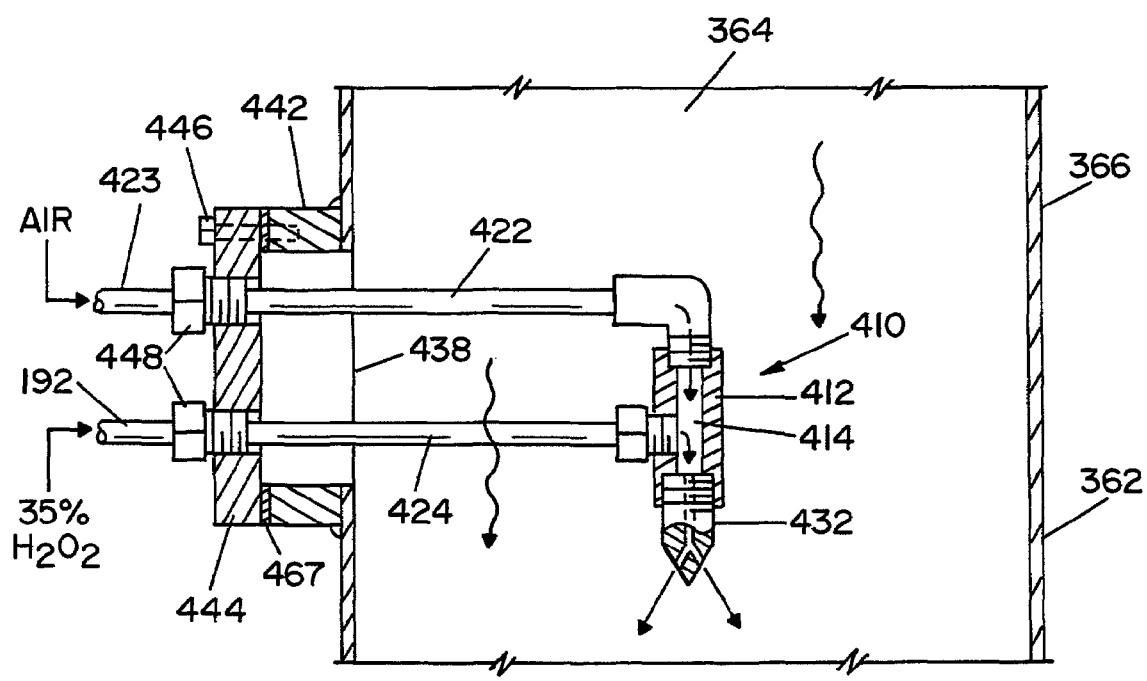
FIG. 8 is an enlarged view of an atomizer from the vaporizer unit shown in FIG. 7.

Injection system 410, best seen in FIG. 8, is comprised of a tubular body 412 that defines an inner mixing chamber 414. An air line 422 and a sterilant line 424 connect to body 412 and communicate with inner mixing chamber 414. Air line 422 is connected to a source (not shown) of filtered, dry pressurized air within system 10 by conduit 423. Sterilant line 424 is connected to sterilant supply line 192 from sterilant supply unit 100. A pump 426, driven by a motor 428, schematically illustrated in FIG. 3, is disposed in sterilant supply line 192 to feed sterilant under pressure into injection system 410. Pump 426 is preferably a variable-speed peristaltic pump. Pump 426 is provided to pump sterilant into injection system 410 at a selected rate. (The injection rate in grams per minute is measured by a mass meter 427.) Motor 428 is preferably a variable speed motor wherein the injection rate of sterilant to injection system 410 can be varied by the speed of motor 428. A pressure sensor 429 is disposed in sterilant supply line 192, downstream from pump 426. Pressure sensor 429 monitors (and ensures) proper sterilant injection rate and ensures that the injection system 410 does not become obstructed.

An atomizing nozzle 432 is attached to body 412. Nozzle 432 is preferably capable of creating a fine spray of sterilant, i.e., namely a mist that is sufficiently small to ensure complete vaporization. A commonly available atomizing nozzle finds advantageous application in the present invention.

To facilitate positioning injection system 410 within vaporizer plenum 364, an opening 438 is formed in the side of shell 366. A collar 442 is attached, preferably by welding, to shell 366 to surround opening 438. A cover plate 444 is attached to collar 442 with conventional fasteners 446. A gasket 467 is disposed between cover plate 444 and collar 442 to provide a complete seal. Threaded openings in cover plate 444 receive conventional fittings 448 that connect air line 422 to an air conduit 423, and sterilant line 424 to sterilant supply line 192.

According to one aspect of the present invention, nozzle 432 is dimensioned relative to shell 366 such that contact of spray from nozzle 432 with shell 366 is minimized or avoided during operation of vaporizer 360.

A temperature sensor 452 is disposed within vaporizer plenum 364 between first end 366a of vaporizer 360 and sterilant injection system 410. A second temperature sensor 454 is disposed within vaporizer plenum 364 downstream from sterilant injection system 410 near second end 366b of vaporizer housing 362. The temperature drop between sensors 452, 454 is proportional to the heat necessary to vaporize the sterilant, as shall be discussed in greater detail below.

A vaporized hydrogen peroxide sensor 462, that is capable of providing an indication of the concentration of vaporized hydrogen peroxide and water vapor, is optionally disposed within vaporizer plenum 364 downstream from sterilant injection system 410. Vaporized hydrogen peroxide sensor 462 is disposed near second end 366b (the outlet end) of vaporizer 360. Sensor 462 is preferably an infrared (IR) sensor, and more preferably a near infrared (IR) sensor. Sensor 462 is generally cylindrical in shape, and is mounted in housing 362 to traverse plenum 364. Sensor 462 is mounted to housing 362 to be easily removable therefrom.

Decontamination Chambers 500A, 500B

As illustrated in FIG. 1, vaporizer unit 300A, 300B are connected respectively to decontamination chambers 500A, 500B by vaporized hydrogen peroxide conduits 512A, 512B. Decontamination chambers 500A and 500B are essentially identical, and therefore, only decontamination chamber 500A shall be described, it being understood that such description applies equally to decontamination chamber 500B.

Figure 6:
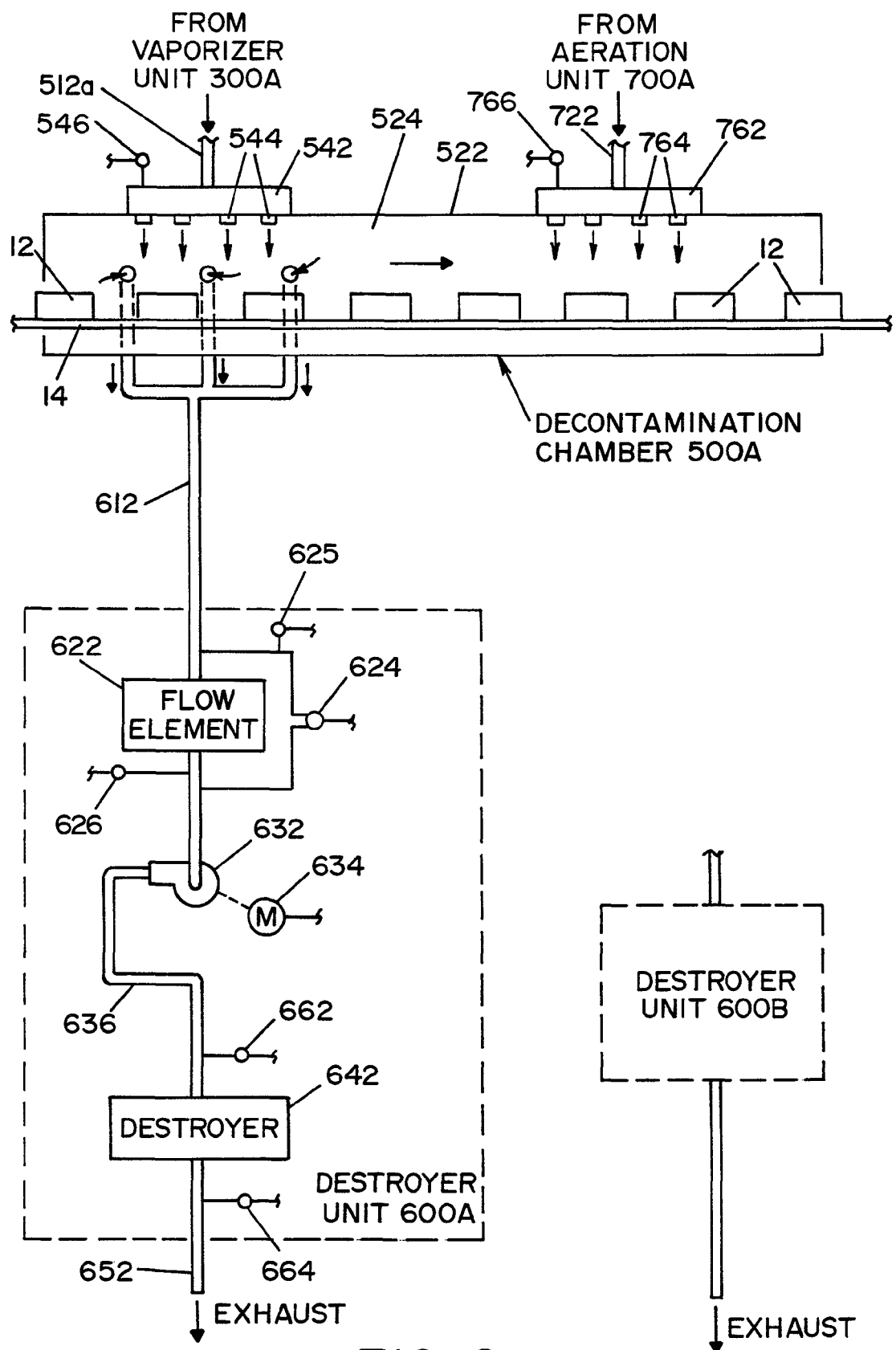
FIG. 6 is a drawing schematically illustrating a destroyer unit from the decontamination system shown in FIG. 1.
Figure 9:
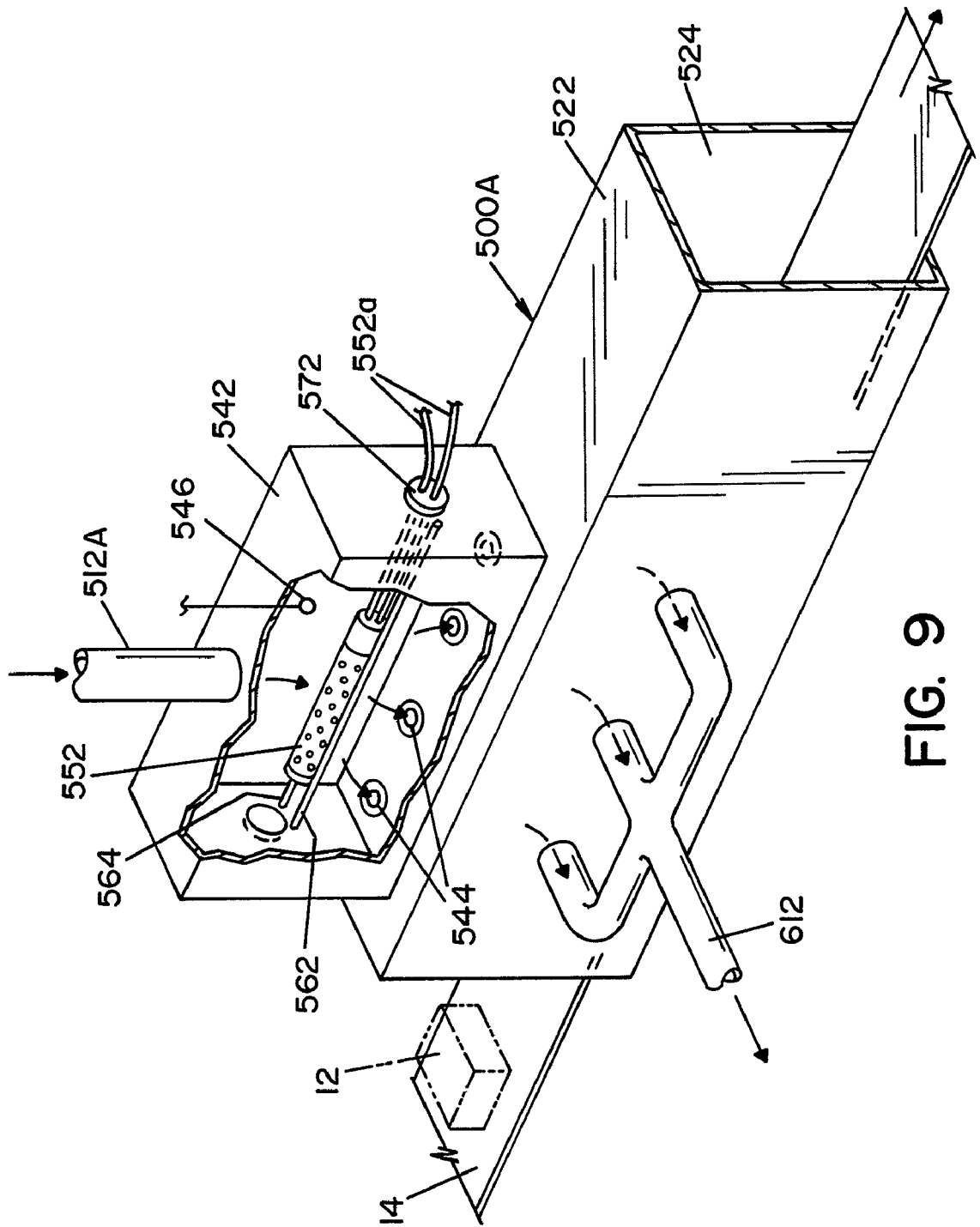
FIG. 9 is a perspective view of a manifold and decontamination chamber.

Decontamination chamber 500A, best seen in FIGS. 6 and 9, is comprised of an enclosure or housing 522 that defines a space or region 524 through which articles 12 to be sterilized/decontaminated are conveyed by conveyor 14. A manifold 542 is mounted on housing 522, and has a plurality of spaced-apart openings or nozzles 544 that communicate with space or region 524 in housing 522. As best seen in FIG. 9, nozzles 544 are disposed above conveyor 14 to uniformly distribute vaporized hydrogen peroxide over articles 12 moving through decontamination chamber 500A.

As best seen in FIG. 9, a temperature sensor 546 and a vaporized hydrogen peroxide sensor 552 are disposed within manifold 542. Vaporized hydrogen peroxide sensor 552 is capable of providing an indication of the concentration of vaporized hydrogen peroxide and water vapor. Sensor 552 is preferably a near infrared (IR) sensor. Sensor 552 is cylindrical in shape and has fiber optic cables 552a extending therefrom. To facilitate easy insertion and removal of near infrared sensor 552 from manifold 542, a pair of spaced-apart rails 562, 564 extend through manifold 542. In the embodiment shown, rails 562, 564 are cylindrical rods. Near infrared sensor 552 is inserted through the opening in the sides of manifold 542. Caps or plugs 572 that allow cables 552a to extend therethrough seal the openings.

Destroyer Units 600A, 600B

Referring now to FIG. 6, destroyer units 600A and 600B are schematically illustrated. Destroyer unit 600A and destroyer unit 600B are essentially identical, and therefore, only destroyer unit 600A shall be described, it being understood that such description applies equally to destroyer unit 600B.

A conduit 612 connects enclosure 522 to destroyer unit 600A. As best seen in FIG. 9, a conduit 612 communicates with region 524 in enclosure 522 through one side of enclosure 522. A flow measuring device 622 is disposed within conduit 612 to provide data with respect to flow therethrough. In the embodiment shown, flow measuring device 622 includes a pressure sensor 624 that is operable to sense a pressure difference across flow measuring device 622 and to provide a signal indicative of flow through device 622. In a preferred embodiment, flow measuring device 622 is a Venturi device. An additional pressure sensor 625 is provided to measure static pressure in the flow measuring device 622, for mass flow calculations as shall be discussed below. A temperature sensor 626 is disposed within conduit 612 downstream from flow measuring device 622. Conduit 612 is connected to the inlet end of a blower 632 that is driven by a motor 634. A conduit 636 extending from the outlet side of blower 632 is connected to a destroyer 642. Destroyer 642 is basically a catalytic device that is operable to destroy hydrogen peroxide flowing therethrough. In this respect, catalytic destroyers convert the vaporized hydrogen peroxide into water and oxygen. A temperature sensor 662 is disposed in front, i.e., upstream, of destroyer 642. A second sensor 664 is disposed behind, i.e., downstream, from destroyer 642.

Aeration Units 700A, 700B

Figure 4:
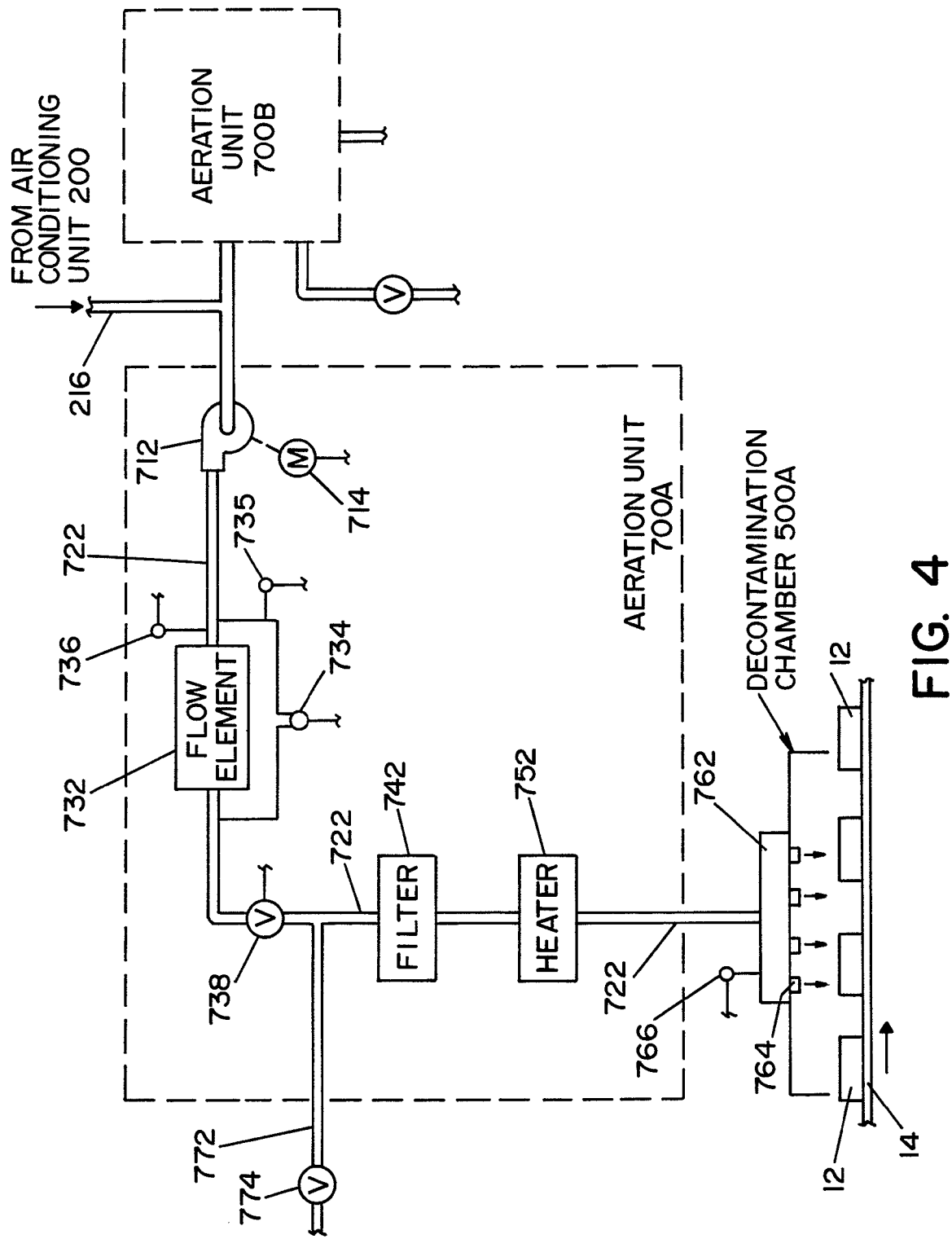
FIG. 4 is a drawing schematically illustrating an aeration unit from the decontamination system shown in FIG. 1.

Referring now to FIG. 4, aeration unit 700A is schematically illustrated. Aeration unit 700A and aeration unit 700B are essentially identical, and therefore, only aeration unit 700A shall be described, it being understood that such description applies equally to aeration unit 700B. As illustrated in FIG. 4, aeration unit 700A is connected to air supply line 216 from air conditioning unit 200. Air supply line 216 from air conditioning unit 200 supplies filtered air to aeration units 700A, 700B. Air supply line 216 is connected to the inlet side of a blower 712 that is driven by a variable-speed motor 714. Blower 712 is disposed within aeration unit 700A to draw air external to system 10 through filter 222 in air conditioning unit 200 and through supply line 216. The outlet side of blower 712 is connected to an aeration conduit 722. Aeration conduit 722 extends through aeration unit 700A. Downstream from blower 712, a flow measuring device 732 is disposed within aeration conduit 722. In a preferred embodiment, flow measuring device 732 is a Venturi device. A pressure sensor 734 measures the pressure difference across flow measuring device 732 that provides signals indicative of the flow through aeration conduit 722. A pressure sensor 735 is provided to measure the static pressure to flow measuring device 732, to facilitate calculation of the mass flow rate through aeration conduit 722. A temperature sensor 736 is disposed before (upstream of) flow measuring device 732. Temperature sensor 736 is disposed between blower 712 and flow measuring device 732. A valve element 738 is disposed in aeration conduit 722 downstream from flow measuring device 732 to regulate the amount of flow through aeration conduit 722. A filter element 742 is disposed downstream from valve element 738. Filter element 742, preferably a HEPA filter, provides a second filtration of the air flowing through aeration conduit 722, in addition to filter 222 in air conditioning unit 200. A heating element 752 is disposed in aeration conduit 722 downstream from filter element 742. Manifold 762 includes a plurality of nozzles or ports 764 to distribute the filtered and heated air into chamber 500A. Manifold 762 is disposed above conveyor 14 at a location where conveyor 14 exits decontamination chamber 500A. A temperature sensor 766 is disposed within manifold 762.

Aeration unit 700A basically provides heated, filtered air to decontamination chamber 500A to purge peroxide vapor from articles 12 on conveyor 14 and to prevent condensation.

As best seen in FIGS. 1 and 4, a conduit 772 connects vaporized hydrogen peroxide conduit 512A to aeration conduit 722. Conduit 772 is connected to vaporized hydrogen peroxide conduit 512A between vaporizer 360 and manifold 542. Conduit 772 is connected to aeration conduit 722 between valve 738 and filter element 742. A valve 774 is disposed in conduit 772 to control flow therethrough. Conduit 772 is provided to periodically decontaminate filter element 742 in aeration unit 700A. By closing valve 738 in aeration conduit 722 and by opening valve 774 in conduit 772, vaporized hydrogen peroxide can be directed from vaporizer 360 through filter element 742.

As provided in the present invention, by controlling the air temperature, air flow rate, sterilant temperature and sterilant injection rate in a decontamination system, a desired concentration of vaporized hydrogen peroxide can be maintained within a decontamination chamber. When using vaporized hydrogen peroxide (VHP) in a decontamination system, it is necessary to prevent the vaporized hydrogen peroxide from condensing on the products or articles to be decontaminated. In a steady state, steady flow vaporized hydrogen peroxide process, the sterilant injection rate, the air flow rate and the air temperature must be controlled to prevent condensation. According to the present invention, the hydrogen peroxide vaporizer system is controlled to a desired vaporized hydrogen peroxide concentration and temperature, to prevent condensation. According to one aspect of the present invention, the operation of system 10 is controlled to maintain the concentration of hydrogen peroxide in an air stream at a dew point temperature that is below the temperature of articles to be decontaminated. System 10 is controlled based upon a mathematical model that shall now be described.

It is known that the dew point concentration of a water and hydrogen peroxide sterilant is dependant on the temperature of the air—into which the sterilant is injected—and the concentration of the water and peroxide in the air. In the case of a steady state, steady flow process, as is used with vaporized hydrogen peroxide decontamination equipment, the dew point concentration is dependant on the injection rate of the sterilant and the temperature and the volumetric flow of air past the injector.

The concentration of hydrogen peroxide $C_p$ in the air stream (mg/liter) can be determined by the following equation:

$$C_p = \frac{I*1000}{F*28.32}\left(\frac{P}{100}\right)E \tag{1}$$

where:

I=sterilant injection rate (grams/min)

F=air flow rate (actual $ft^3$/min)

P=percent of peroxide in sterilant

E=vaporizer efficiency (0.90=90%) which is a function of the amount of hydrogen peroxide broken down in the vaporization process.

In the equation, the 1000 is a conversion factor for converting grams to milligrams. The 28.32 is a conversion factor for converting cubic feet to liters.

The concentration of water vapor $C_w$ in the air stream (mg/liter) can be determined by the following equation:

$$C_w = \frac{I*1000}{F*28.32}\left(\frac{100-P}{100}\right) + \frac{I*1000}{F*28.32}\left(\frac{P}{100}\right)(1-E)\frac{9}{17} + C_{w,air} \tag{2}$$

Hydrogen peroxide breaks down into water and oxygen. Nine-seventeenths of the catalyzed hydrogen peroxide is converted into water with the balance being converted to oxygen. This is seen in equation 2 which adds the water portion of the catalyzed hydrogen peroxide to the concentration of water seen in the air stream.

$C_{w,air}$=concentration of water in the air stream flowing into the vaporizer (mg/liter)

From equations (1) and (2), the concentration of water and hydrogen peroxide in the air stream can be determined. The dew point of the hydrogen peroxide is determined based on the following.

It is known that when liquid of a given concentration of $H_2O_2$ is placed in an enclosure with no initial humidity, the liquid hydrogen peroxide and water will evaporate and reach equilibrium in the enclosure. The concentration of the hydrogen peroxide vapor will be lower than hydrogen peroxide concentration found in the liquid. From known sources, such as a book entitled: "Hydrogen Peroxide" by Schumb, Satterfield, & Wentworth ©1955, equations and a table provide the relationship between the liquid and gas concentrations for $H_2O_2$ and water. Within an enclosure, the vapor concentration will reach the saturation point.

Source information is used to determine the saturation point of water and hydrogen peroxide mixtures in a given volume.

In this respect, the mole fraction of hydrogen peroxide in phase gas ($y_h$) over a hydrogen peroxide-water solution (liquid form) is given by the following equation.

$$y_h = \frac{p_{hg} x_h \gamma_h}{P} = \frac{p_{hg} x_h \gamma_h}{(p_{wg} x_w \gamma_w) + (p_{hg} x_h \gamma_h)} \quad (3)$$

where:
$x_h$=Mole fraction of hydrogen peroxide in liquid sterilant
P=Total vapor pressure of the mix (mm Hg).
The total vapor pressure (P) of the mix is determined by the following equation.

$$P = p_{wg} x_w \gamma_w + p_{hg}(1 - x_w) \gamma_h$$

where:
$p_{wg}$=Vapor pressure of water (mm Hg) (see equation below)
$x_w$=mole fraction of water
$p_{hg}$=Vapor pressure of hydrogen peroxide (mm Hg) (see equation below)
$\gamma_w$=Activity coefficient for water
The activity coefficient for water is determined by the following equation.

$$\gamma_w = \exp\left(\frac{(1-x_p)^2}{RT}[B_o + B_1(1-4x_w) + B_2(1-2x_w)(1-6x_w)]\right) \quad (5)$$

where:
$x_p$=mole fraction of hydrogen peroxide
R=1.987 cal/gmole-K ideal gas constant
$B_o$=Coefficient for calculation of activity coeff.=−1017÷0.97*T
$B_1$=Coefficient for calculation of activity coeff.=85
$B_2$=Coefficient for calculation of activity coeff.=13
T=Water vapor temperature (K)
The activity coefficient for hydrogen peroxide ($\gamma_h$) is determined by the following equation.

$$\gamma_h = \exp\left(\frac{(x_w)^2}{RT}[B_o + B_1(3-4x_w) + B_2(1-2x_w)(5-6x_w)]\right) \quad (6)$$

The mole fraction of hydrogen peroxide ($x_p$) is determined by the following equation (taken from H2O2.com).

$$x_p = (\text{Percent} * MW_w)/(MW_p * (100 - \text{Percent}) + \text{Percent} * MW_w) \quad (7)$$

where:
Percent=Percent hydrogen peroxide in gas or liquid form.
$MW_w$=Molecular weight of water=18.016 grams/mole.
$MW_p$=Molecular weight of hydrogen peroxide=34.016 grams/mole.

The vapor pressure of water is determined using the following equations (from the ASHRAE Fundamentals book). For temperatures above 32° F., the following equation is given:

$$VP = \text{Exp}[(C_8/(TF+460)] + C_9 + C_{10}*(TF+460) + C_{11}*(TF+460)^2 + C_{12}*(TF+460)^3 + C_{13}*\text{Log}(TF+460)) \quad (8)$$

where:
VP=Vapor pressure at saturation (psi)
TF=Vapor temperature (° F.)
$C_8$=−10440.397
$C_9$=−11.29465
$C_{10}$=−0.027022355
$C_{11}$=0.00001289036
$C_{12}$=−2.4780681E-09
$C_{13}$=6.5459673

The vapor pressure of anhydrous hydrogen peroxide is determined by the following equation.

$$p_{hg} = 10^{(44.5760 - \frac{4026.3}{T} - 12.996 \log T + 0.0046055T)} \quad (9)$$

where:
$p_{hg}$=Vapor pressure of hydrogen peroxide (mm Hg)
T=Vapor temperature (K)
The ideal gas law can be used to calculate the saturation level of the hydrogen peroxide and water vapor components at a given temperature, as shown in reference 2. The ideal gas law is determined by the following equation.

$$PV = nRT \quad (10)$$

where:
P=Vapor pressure of water and peroxide mix (mm Hg).
V=Volume (m³)
n=Number of moles
R=Universal Gas Constant (0.082 liter-atm/mole-K)
T=Temperature of vapor (K)
The saturated concentration of peroxide or water vapor is usually given in mass per unit volume. Equation (10) can be arranged to determine concentration as given in equation (11) below.

$$C = w/V = Mn/V = M \times P/(RT) \quad (11)$$

where:
C=Saturated Concentration of vapor (mg/liter)
w=Mass (mg)
V=Volume (liter)

M = molecular weight of water or hydrogen peroxide (grams/mole).

= 34.016 grams/mole for peroxide

= 18.016 grams/mole for water x=Vapor mole fraction.
P=Vapor pressure of water and peroxide mix (mm Hg) from equations (8) and (9).

R=Universal Gas Constant (0.082 liter-atm/mole-K)
T=Temperature of vapor (K)

Equation (11) can be solved for the saturated concentration of water ($C_{w,sat}$) and hydrogen peroxide ($C_{h,sat}$). The percent of hydrogen peroxide vapor can be calculated using the following equation.

$$P_c = [C_{p,c}/(C_{p,c}+C_{w,c})]100 \quad (12)$$

where:
$P_c$=Percent hydrogen peroxide in vapor form.
$C_{p,c}$=Concentration of hydrogen peroxide from equation (11) (mg/liter)
$C_{w,c}$=Concentration of water from equation (11) (mg/liter)

The percent of hydrogen peroxide in vapor form calculated with equation (12) can be compared to the percent of hydrogen peroxide calculated using equations (1) and (2).

$$P = [C_p/(C_p+C_w)]100 \quad (13)$$

where:
P=Theoretical percent of hydrogen peroxide in air stream.
$C_p$ & $C_w$ are explained in equations (1) and (2) above.

The percent of peroxide calculated in equation (12) should match that calculated in equation (13). As explained above, if the percentage of hydrogen peroxide in the sterilant is used in equation (7), the percentage found using equation (12) will be too low. The equations can be forced to produce the correct saturated vapor concentration from equation (12) by increasing the concentration (Percent) of liquid hydrogen peroxide used in equation (7) until the concentration found using equations (12) and (13) match.

Inlet air temperature must be sufficient to vaporize the sterilant and provide an outlet temperature high enough to prevent condensation downstream. The required temperature at the inlet to the vaporizer tube is determined as follows.

Figure 10:
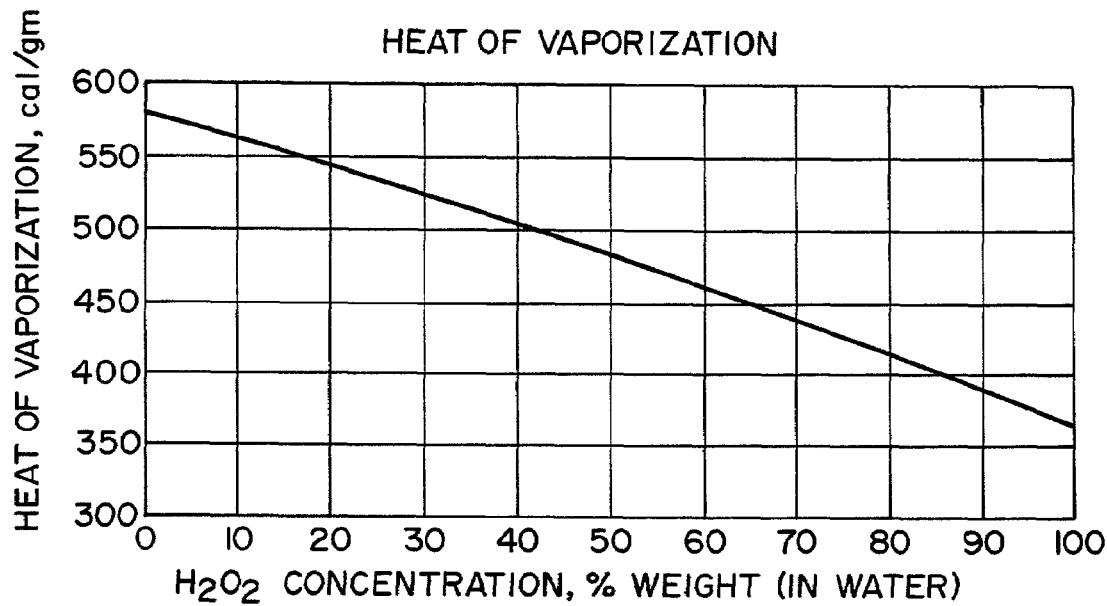
FIG. 10 is a graph of a heat of vaporization (latent heat) as a function of a concentration of hydrogen peroxide in water.

The heat required to vaporize the hydrogen peroxide is mostly due to the latent heat of vaporization for the hydrogen peroxide. To a smaller extent, the sensible heat is needed to heat the liquid sterilant from room temperature to vaporization temperature. The heat of vaporization (latent heat) as a function of the concentration of hydrogen peroxide in water is given in FIG. 10, provided courtesy of H2O2.com.

The latent heat, $h_{fg}$, is given in units of calories per gram. The units for $h_{fg}$ can be converted to BTU per gram for 35% peroxide in water as follows.

$$h_{fg} = 525 \frac{cal}{gm}\left(\frac{1\,BTU}{251.9968\,cal}\right) = 2.083 \frac{BTU}{gm}$$

The heat of vaporization is determined by the following equation.

$$Q_{vap} = h_{fg}(I) \text{ (BTU/min)} \quad (14)$$

where:
I=sterilant injection rate (grams/min)

The sensible heat required to heat the sterilant from room temperature to the desired outlet temperature is determined by the following equation.

$$Q_{sen} = I \cdot \rho_{ster} \cdot C_{p,ster}(T_2 - T_{amb}) \quad (15)$$

where:
$\rho_{ster}$=density of the sterilant found from H2O2.com (see FIG. 11) (gram/ml)
$C_{p,ster}$=specific heat of sterilant found from H2O2.com (see FIG. 12) (BTU/gram-C)
$T_2$=vaporizer outlet temperature defined by user (C)
$T_{amb}$=ambient temperature of sterilant (C)

Figure 11:
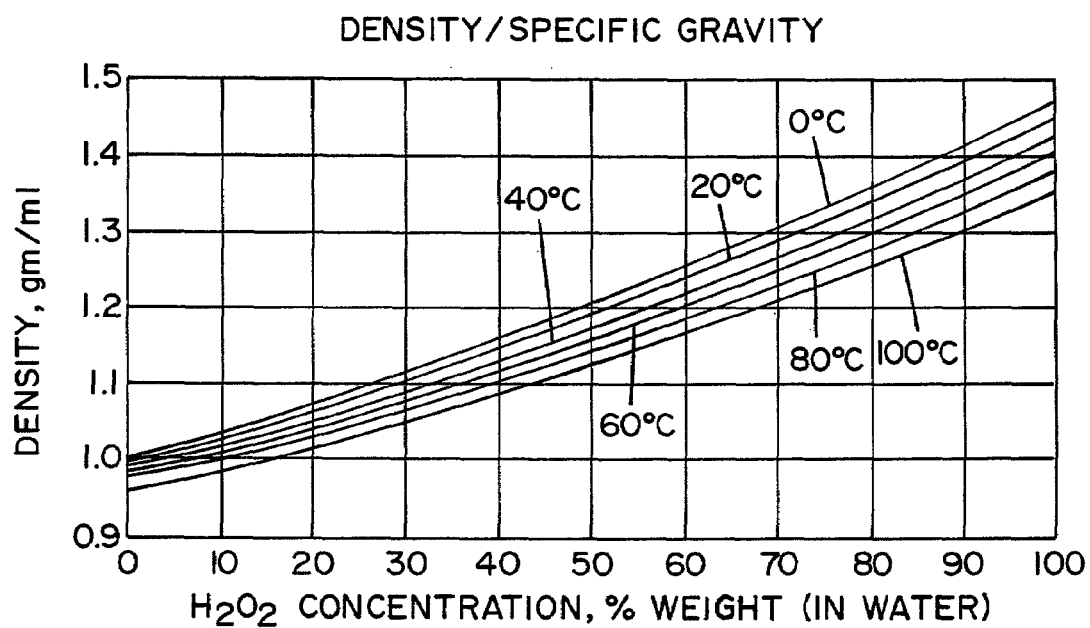
FIG. 11 is a graph of density of hydrogen peroxide as a function of a concentration of hydrogen peroxide in water.
Figure 12:
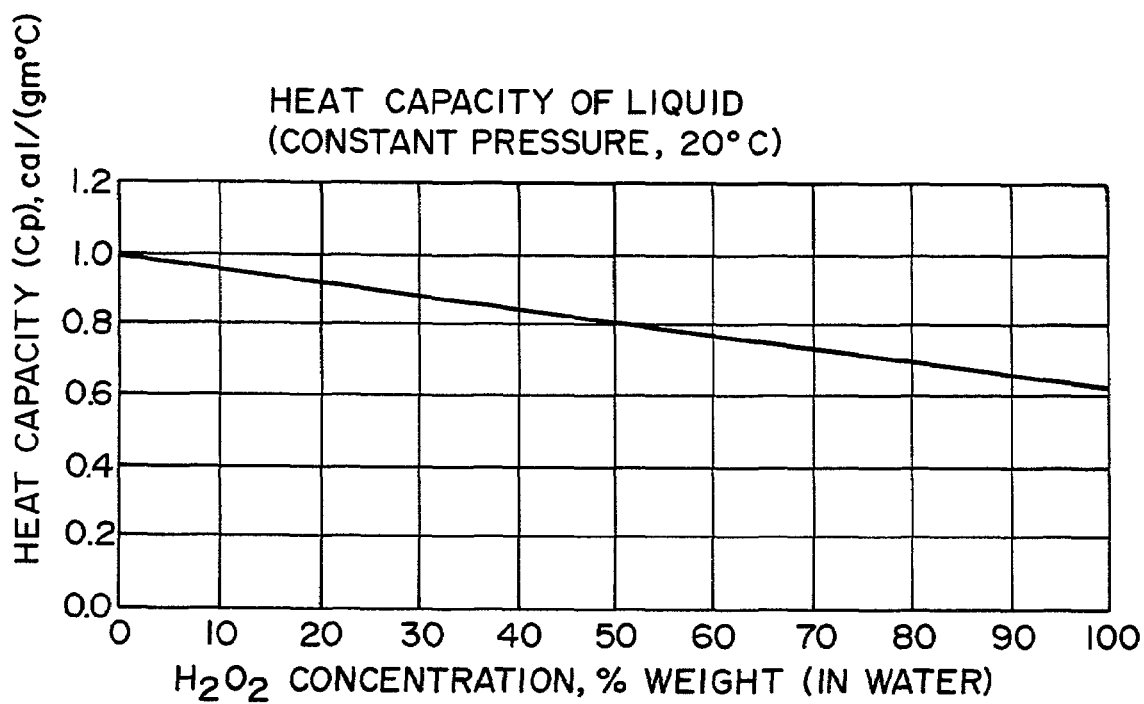
FIG. 12 is a graph of a heat capacity of hydrogen peroxide as a function of a concentration of hydrogen peroxide in water.

FIGS. 11 and 12 are provided courtesy of H2O2.com.

Hot air will be used to vaporize the sterilant. The heat lost by the air stream, $Q_{air}$, is determined by the following equation.

$$Q_{air} = \dot{m} \cdot C_p \cdot (T_1 - T_2) \text{ (BTU/min)} \quad (16)$$

where:
$\dot{m}$=air mass flow rate=(0.075 lbm/scf)×scfm (lbm/min)
$C_p$=specific heat of air at the bulk temperature (BTU/lbm-R)
$T_1$=inlet air temperature (into vaporizer tube) (° F.)
$T_2$=outlet air temperature (out of vaporizer tube) (° F.)

The outlet temperature is determined by knowing the dew point of the sterilant in the air stream using the equations given above. The value for $Q_{air}$ is equal to $Q_{vap}$ plus $Q_{sen}$. The only unknown in equation (16) is the inlet temperature. Solving equation (16) for $T_1$ gives:

$$T_1 = \frac{Q_{vap} + Q_{sen}}{\dot{m} \cdot C_p} + T_2 \quad (17)$$

Referring now to the operation of system 10, a controller (not shown) is programmed to allow system 10 to operate in three different modes of operation, namely: (1) operating to maintain a desired dew point temperature within decontamination chambers 500a, 500b, (2) operating at a fixed rate of sterilant injection, and (3) operating so as to hold a desired peroxide concentration. The controller receives input signals from the various sensors throughout system 10. In addition, the controller is programmed, based upon the foregoing equations, to control the heating elements 298, 352, 752, blower motors 294, 322, 632, 712, and pump motors 124, 324, 428 in accordance with a selected mode of operation.

Referring first to the first mode of operation that maintains a specific dew point in the decontamination chambers, certain user inputs are required for this mode of operation. Specifically, the user inputs the following: (a) a desired dew point temperature ($T_{dp}$), (b) a desired vaporizer outlet temperature, and (c) the percent of hydrogen peroxide in the liquid sterilant.

When vaporized hydrogen peroxide sensor 552 is used, the dew point can be calculated. When no sensor is available, it may be estimated using equations (1) and (2) to calculate the water and peroxide concentrations (assuming efficiency is known).

As is known by those skilled in the art, a dew point temperature is the temperature at which water vapor and hydrogen peroxide vapor in the air become saturated and condensation begins. In the context of the present invention, the objective of system 10 when operated in the first mode of operation is to control the air temperature, air flow, and concentration of water and vaporized hydrogen peroxide (VHP) in the air stream so as to prevent condensation on articles 12 to be sterilized. As will be appreciated by those skilled in the art, the temperature of articles 12 to be sterilized is a factor in determining an actual dew point temperature. In the embodiment shown, articles 12 are to be conveyed through a decontamination chamber 500A or 500B. The initial temperature of articles 12 entering chamber 500A or 500B is important in determining the desired dew point temperature ($T_{dp}$). The desired dew point temperature is determined based upon the initial temperature of articles 12 entering decontamination chamber 500A or 500B. To ensure that condensation does not form on articles 12, "the desired dew point temperature," also referred to as a "pre-selected temperature," inputted into the system is preferably a specific number of degrees lower than the initial temperatures of articles 12 when entering decontamination chamber 500A or 500B. In a preferred embodiment, the desired dew point temperature is selected to be approximately 30° C. lower than the initial temperature of articles 12 when entering decontamination chamber 500A or 500B. It will, of course, be appreciated that the added temperature factor could be increased or decreased, so long as it remains lower than the initial temperature of articles 12.

As will be appreciated by those skilled in the art, the lower the temperature of articles 12 to be sterilized when entering the decontamination chamber, the lower the dew point temperature at which the water and hydrogen peroxide vapor will condense on articles 12.

The second piece of data inputted by the user is a desired vaporizer outlet temperature. To a certain extent, these data are also dependent on the physical properties of articles 12 to be decontaminated. In this respect, it may be necessary to operate system 10 below a certain temperature to avoid damaging articles 12.

The third piece of data inputted by the user is the percent of hydrogen peroxide in the liquid sterilant. This information is provided by the supplier of the liquid sterilant.

Based upon the foregoing inputted information, the system operates in the first mode of operation as follows.

Initially, both reservoir tanks 132A, 132B in sterilant supply unit 100 are preferably filled with liquid sterilant. Liquid sterilant is provided to the respective tanks by pump 122. Tanks 132A, 132B are preferably filled to a desired fill level, indicated by level sensor 154 in each tank 132A, 132B.

Preferably, one tank 132A or 132B is used to provide liquid sterilant to vaporizer units 300A, 300B at any one time. Once a given tank 132A or 132B is depleted of liquid sterilant, liquid sterilant from the other tank 132A or 132B is then used to supply vaporizer units 300A, 300B. An empty tank 132A or 132B can be refilled by opening the appropriate valves 144, 146 to empty tank 132A or 132B and by pumping liquid sterilant from external supply 114 into the empty tank. While an empty tank 132A or 132B is being filled, the other tank 132A or 132B is used to supply vaporizer units 300A, 300B. Tanks 132A, 132B are dimensioned to allow continued operation of decontaminating system 10 while a tank 132A or 132B is being refilled. As a result, a generally continuous flow of sterilant can be provided simultaneously to vaporizers 300A, 300B to allow continuous processing of articles 12.

As illustrated in FIG. 2, liquid sterilant from tanks 132A, 132B are directed to holding tank 170. Holding tank 170 is dimensioned to allow any gases that may have been released from the liquid sterilant to be vented from supply unit 100 prior to entering vaporizer units 300A, 300B. In this respect, it has been found that the outer dimensions of holding tank 170, being significantly larger than the feed lines and conduit in system 10, allows gas in the liquid sterilant to be released and vented, and prevents such gas bubbles or pockets from flowing to vaporizer units 300A, 300B.

As previously indicated, sterilant supply unit 100 is a gravity-feed system. To avoid trapping gas bubbles in vaporizer feed line 192, all conduit and piping forming vaporizer feed line 192 from holding tank 170 to vaporizer units 300A, 300B have a downward slope such that any gas released by the liquid sterilant within vaporizer feed line 192 migrates to holding tank 170 where it can be released through vent line 174. Valve 176 in vent line 174 is controlled by float switch 177.

Referring now to the operation of vaporizer units 300A, 300B as shown in FIG. 3, the operation of vaporizer unit 300A shall now be described, it being understood that such description applies also to vaporizer unit 300B. The controller of system 10 causes motor 324 to drive blower 322, thereby drawing air through the air-conditioning unit 200 and blowing the air into vaporizer 360 through vertical conduit 328. The air flow created by blower 322 is measured by flow element 332. As indicated above, motor 324 is preferably an electrically-controlled variable-speed motor wherein the air flow created through vaporizer 360 can be adjusted automatically by the controller. Heating element 352 is energized to heat the air entering vaporizer plenum 364. The output of heating element 352 may be adjusted by varying the duty cycle to heating element 352. In other words, the temperature of the air flowing into vaporizer plenum 364 can be adjusted by adjusting the output of heater element 352.

When system 10 is initially started up, air from blower 322 is forced through plenum 364 and through decontamination chamber 500A. Heated air is blown through system 10 to allow components thereof to heat up until the temperature of system 10 stabilizes. Temperature sensors 274, 286, 336, 452, 454, 546, 626, 662 and 664 throughout system 10 monitor the temperature of the air within system 10 and determine when the system has reached an equilibrium temperature based upon the input temperature of heating element 352 as measured by temperature sensor 336.

Once the temperature of system 10 has stabilized, liquid sterilant is injected into the heated air stream by injector system 410. The amount of sterilant injected into the system is established by the controller based upon calculations using the equations set forth above. The initial injection of liquid sterilant into the heated stream creates a pressure increase within vaporizer plenum 364 as a result of the liquid sterilant vaporizing in the heated air stream. This increase in pressure within vaporizer plenum 364 will result in reduced air flow into vaporizer 360. This drop in air flow will be sensed by flow element 332. In accordance with one aspect of the present invention, the operation of blower motor 322 is controlled by the sensed air flow through flow element 332. Based upon output signals from flow element 332 and sensor 334, the controller increases the speed of blower 322 to maintain the desired air flow through vaporizer plenum 364 and the downstream units. In this respect, system 10 is self-adjusting to maintain a desired air flow rate through system 10 while vaporized hydrogen peroxide is being generated. The vaporized hydrogen peroxide from vaporizer unit 360 is conveyed into decontamination chamber 500A through peroxide feed line 512A. In accordance with another embodiment of the present invention, for safety reasons vaporizer unit 360 is located above decontamination chamber 500A, as shown in FIG. 3. In this respect, any hydrogen peroxide not vaporized in vaporizer unit 360 will remain in a liquid state and drip or flow downward into decontamination chamber 500A. The dripping or flowing of liquid hydrogen peroxide into decontamination chamber 500A may be ascertained from a visual inspection of decontamination chamber 500A. If liquid hydrogen peroxide is noticed in decontamination chamber 500A, the system is shut down to avoid a hazardous condition.

The vaporized hydrogen peroxide enters manifold 542 where it is dispensed over the articles 12 through nozzles 544. In this respect, as will be appreciated, articles 12 begin to move through decontamination chamber 500A once steady-state operation of vaporizer 360 has been established.

As schematically illustrated in the drawings, the vaporized hydrogen peroxide is directed over articles 12 from above. Blower 632 in destroyer unit 600A is energized to draw the vaporized hydrogen peroxide out of decontamination chamber 500A through line 612. Flow element 622 provides signals indicative of the flow to blower 632. The controller controls the operation of blower 632 so as to balance the air flow out of decontamination chamber 500A with the flow of air through vaporizer plenum 364. The air stream drawn from decontamination chamber 500A is forced through destroyer 642 where the vaporized hydrogen is broken down into oxygen and water that is exhausted from system 10, as schematically illustrated in FIG. 6.

As indicated above, during this mode of operation, i.e., wherein the system is controlled to maintain the concentration of water vapor and vaporized hydrogen peroxide in decontamination chamber 500A at a desired dew point temperature, the controller of system 10 constantly monitors the various sensors throughout system 10 to ensure that the proper amount of liquid hydrogen peroxide sterilant is being injected into injection system 410.

In accordance with another aspect of the present invention, system 10 monitors and verifies the amount of vaporized hydrogen peroxide produced within system 10 in several ways. According to a first method of measuring the vaporized hydrogen peroxide (VHP), system 10 monitors the temperature drop across destroyer 642 using temperature sensors 662 and 664. In this respect, the destruction of vaporized hydrogen peroxide produces heat. By monitoring the change in temperature across destroyer 642, a first indication of the amount of vaporized hydrogen peroxide flowing through the system can be determined.

A second method of measuring and monitoring the vaporized hydrogen peroxide within system 10 is through measurements from vaporized hydrogen peroxide sensor 462 or 552.

A third method of measuring and monitoring the amount of vaporized hydrogen peroxide in system 10 is by monitoring the injection rate of liquid sterilant into injection system 410. In this respect, the output of mass meter 427 can be monitored to provide an indication of the metered amounts of liquid sterilant to injection system 410. The peroxide and water concentrations are calculated using equations 1 and 2.

A fourth method of measuring and monitoring the amount of vaporized hydrogen peroxide in system 10 is to monitor the temperature change within vaporizer plenum 364. Specifically, temperature sensors 452 and 454 within vaporizer plenum 364 are monitored. Just as the destruction of vaporized hydrogen peroxide produces a specific amount of heat per unit mass, so, too, does the vaporization of liquid hydrogen peroxide require a specific amount of heat which produces a decrease in temperature. By monitoring the change in temperature in the air stream within vaporizer plenum 364, the amount of vaporized hydrogen peroxide in system 10 can be determined.

In accordance with one aspect of the present invention, system 10 monitors all four of the foregoing conditions and compares the output calculations to each other. If any one of the four monitored parameters is outside an acceptable range of error, system 10 alerts the system operator of potential problems.

By continuously monitoring the sensors throughout system 10, the concentration of water vapor and hydrogen peroxide vapor within the air stream can be maintained at a desired dew point temperature. Since, as indicated above, the desired operating dew point temperature is preferably approximately 30° C. below the temperatures of articles 12 entering the decontamination chamber, condensation on such articles 12 can be avoided.

The present invention thus provides a system 10 that can operate to maintain a specific dew point temperature, to prevent water vapor or vaporized hydrogen peroxide from condensating on articles 12 and, at the same time, maintain a desired operating temperature so as not to damage articles 12 to be decontaminated.

Referring now to the second mode of operation, i.e., wherein system 10 is held to a predetermined injection rate, the user is required to once again input a desired manifold 542 temperature, and the percent of hydrogen peroxide in the liquid sterilant. In this mode of operation, once a steady-state flow has been established, the injection rate of injection system 410 is maintained at a set amount. Air flow through the system may increase to maintain a desired operating temperature, however, the injection rate remains constant throughout the operation in this mode. The dew point is supplied to the user so a determination can be made if condensation will occur.

In the third mode of operation, i.e., wherein the vaporized hydrogen peroxide concentration is held steady, the user inputs a desired operating temperature of the manifold 542. Once steady-state air flow has been established through the system, liquid hydrogen peroxide is injected into the air stream. As indicated above, system 10 monitors the amount of vaporized hydrogen peroxide in system 10 and maintains the desired vaporized hydrogen peroxide concentration by increasing or decreasing the injection rate of pump 426 of injection system 410.

The control strategy for the first mode of operation is carried out as follows:

1.) The user inputs the following:
   a. The desired dew point temperature ($T_{dp}$)
   b. The manifold temperature.
   c. The percent hydrogen peroxide in the liquid sterilant
2.) The following is known:
   a. Vaporizer efficiency (E) found through testing. (When a near IR sensor 462 is used, equations 1 and 2 are not required to determine the concentrations of hydrogen peroxide and water. When a near IR sensor 462 is not used, equations 1 and 2 are used to calculate the concentrations of hydrogen peroxide and water. This calculation requires that the efficiency of the vaporizer be inputted by the user into the controller of decontamination system 10.)
   b. Concentration of water in the air stream out of the dryer, from vendor data or from testing.
3.) Initially assume the vapor out of the vaporizer will contain the same percentage of hydrogen peroxide as the liquid sterilant.
4.) Calculate the mole fraction of hydrogen peroxide ($x_p$) in the sterilant using equation 7.
5.) Calculate the mole fraction of water in the sterilant, $x_w = 1 - x_p$
6.) Calculate the activity coefficients using equations 5 and 6 at the dew point temperature input by the user.
7.) Calculate the vapor pressure of water and hydrogen peroxide using equations 8 and 9 at the dew point temperature input by the user.
8.) Calculate the total vapor pressure using equation 4.
9.) Determine the mole fraction of hydrogen peroxide in gas over liquid using equation 3.
10.) Determine if the mole fraction calculated using equation 7 equals that calculated using equation 3.
11.) If the mole fractions don't match within an acceptable error, iterate the mole fraction of peroxide in the sterilant (liquid state) and redo steps 5 through 10 above. One of many iteration techniques may be used to converge to the solution.

12.) If the mole fractions match within the acceptable error, calculate the saturated concentration of the hydrogen peroxide ($C_{h,sat}$) and water ($C_{w,sat}$) using equation 11.

13.) Calculate the sterilant injection rate from equation 1 using $C_{h,sat}$.

14.) Calculate the concentration of water ($C_w$) using equation 2.

15.) Compare $C_w$ with $C_{w,sat}$

16.) If $C_w$ and $C_{w,sat}$ are not equal within an acceptable error, recalculate the percentage of peroxide (P) using $C_{h,sat}$ and $C_w$: $P=C_{h,sat}/(C_{h,sat}+C_w)100$ and redo steps 4 through 15.

17.) If $C_w$ and $C_{w,sat}$ are within acceptable error, the initial injection rate will be set equal to that calculated in step 15 above.

18.) Calculate the heat of vaporization ($Q_{vap}$) using equation 14.

19.) Determine the vaporizer inlet air temperature ($T_1$) using equation 16.

20.) If the air temperature calculated in step 19 is not too great for downstream components, the air flow can be established at $T_1$ and the peroxide can be injected into the air stream after the system has reached steady state.

21.) If the air temperature, $T_1$ is too great for downstream components, the temperature may be initially set to the maximum allowable temperature.

22.) The injection rate can then be determined by iterating until the vaporizer outlet temperature is above the dew point by the same margin as that between the desired dew point temperature ($T_{dp}$) and the desired outlet temperature ($T_2$).

23.) A gradual step-up process can be continued until the required dew point ($T_{dp}$) and outlet ($T_2$) temperatures are achieved.

24.) If feedback is provided to the control, the dew point can be achieved by using the actual concentration of hydrogen peroxide and water instead of those calculated in equations 1 and 2.

The control strategy for the second mode of operation is set forth as follows.

1.) The user inputs the following:
   a. The desired injection rate
   b. The manifold temperature.
   c. The percent hydrogen peroxide in the liquid sterilant 2.) The following is known:
   a. Vaporizer efficiency (E) found through testing (used when near IR sensor is not used).
   b. Concentration of water in the air stream out of the dryer, from vendor data or from testing.

3.) The controller calculates and displays a dew point based upon the injection rate set by the user.

4.) The user, knowing the dew point for the inputted injection rate, can then, if necessary, adjust, i.e., change, the "user inputs" to avoid condensation on the articles to be decontaminated. In this respect, in the second mode of operation, there is no automatic control of the dew point.

The control strategy for the third mode of operation is set forth as follows.

1.) The user inputs the following:
   a. The desired concentration of hydrogen peroxide.
   b. The manifold temperature.
   c. The percent hydrogen peroxide in the liquid sterilant.

2.) The following is known:
   1) Vaporizer efficiency (E) found through testing (used when near IR sensor is not used).
   2) Concentration of water in the air stream out of the dryer, from vendor data or from testing.

3) The controller calculates and steps-up the injection rate of the liquid hydrogen peroxide until the desired concentration of vaporized hydrogen peroxide is achieved.

4) The controller calculates and displays the dew point at desired concentration of hydrogen peroxide The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method of decontaminating articles, comprising the steps of:

(a) moving a plurality of articles having a known temperature along a first path;

(b) conveying a carrier gas along a second path that includes an elongated plenum, said second path intersecting said first path downstream from said plenum;

(c) sensing the volumetric flow of said carrier gas along said second path;

(d) heating said carrier gas moving along said second path to a temperature of at least about 105° C. at a location upstream of said plenum;

(e) introducing into said carrier gas at an injection site in said plenum an atomized mist of a liquid hydrogen peroxide of known concentration to produce vaporized hydrogen peroxide;

(f) sensing a temperature of said carrier gas at a location before said injection site and at a location downstream of said injection site;

(g) determining the concentration of vaporized hydrogen peroxide introduced into said carrier gas based upon the temperatures of said carrier gas before said injection site and downstream of said injection site; and (h) adjusting the concentration of vaporized hydrogen peroxide in said carrier gas by varying the following:
   (1) the volumetric flow of carrier gas along said second path;
   (2) the volume of hydrogen peroxide introduced into said carrier gas; and
   (3) the heating of said carrier gas before said carrier gas is introduced into said plenum, such that the concentration of said vaporized hydrogen peroxide in said carrier gas where said first path intersects said second path has a dew point temperature below said known temperature of said articles.

2. A method as defined in claim 1, further comprising the step of destroying said vaporized hydrogen peroxide along said second path downstream from said first path.

3. A method as defined in claim 1, wherein the concentration of vaporized hydrogen peroxide in said carrier gas is maximized.

4. A method of decontaminating articles, comprising the steps of:

(a) moving a plurality of articles along a first path that includes a decontamination chamber, said articles having a predetermined temperature;

(b) conveying a carrier gas along a second path that includes an elongated plenum and said decontamination chamber, said decontamination chamber being downstream from said elongated plenum;

(c) sensing the volumetric flow of said carrier gas along said second path;

(d) heating said carrier gas moving along said second path to a temperature of about 105° C. at a location upstream of said plenum;

(e) introducing an atomized mist of liquid hydrogen peroxide of a known concentration into said carrier gas at an injection site in said plenum to produce vaporized hydrogen peroxide in said plenum;

(f) sensing a temperature of said carrier gas at a location before said injection site and at a location downstream of said injection site;

(g) determining the concentration of vaporized hydrogen peroxide introduced into said carrier gas based upon the temperatures of said carrier gas before said injection site and downstream of said injection site;

(h) exposing said articles in said decontamination chamber to said vaporized hydrogen peroxide; and (i) controlling said concentration of said vaporized hydrogen peroxide to a temperature at or below a pre-selected temperature by adjusting the following:
   (1) said volumetric flow of carrier gas moving along said second path;
   (2) a rate of introduction of said liquid hydrogen peroxide introduced into said carrier gas; and
   (3) said temperature of said carrier gas introduced into said plenum.

5. A method as defined in claim 4, wherein said pre-selected temperature is about 30° C. below said predetermined temperature of said articles.

6. A method as defined in claim 4, wherein said elongated plenum is vertically aligned and disposed above said decontamination chamber.

7. A method as defined in claim 4, wherein said step (i) includes a step of:
   simultaneously determining a concentration of vaporized hydrogen peroxide in said carrier gas upstream of said decontamination chamber and adjusting a rate of introduction of said liquid hydrogen peroxide into said carrier gas to achieve a predetermined concentration of vaporized hydrogen peroxide in said carrier gas prior to said decontamination chamber.

8. A method as defined in claim 7, further comprising the steps of:
   providing a destroyer in said second path downstream of said decontamination chamber; and
   determining said concentration of vaporized hydrogen peroxide in said carrier gas by measuring a change in temperature across said destroyer.

9. A method as defined in claim 7, further comprising the steps of:
   providing a hydrogen peroxide sensor operable to measure said concentration of vaporized hydrogen peroxide in said carrier gas along said second path; and
   determining said concentration of vaporized hydrogen peroxide in said carrier gas based upon said hydrogen peroxide sensor.

10. A method as defined in claim 9, wherein said hydrogen peroxide sensor is an infrared (IR) sensor.

11. A method as defined in claim 9, wherein said hydrogen peroxide sensor is a near infrared (IR) sensor.

12. A method as defined in claim 9, wherein said hydrogen peroxide sensor is disposed in said decontamination chamber.

13. A method as defined in claim 9, wherein said hydrogen peroxide sensor is disposed in said plenum.

14. A method as defined in claim 7, further comprising the steps of:
   providing a mass meter operable to measure an injection rate of said liquid hydrogen peroxide into said plenum; and
   determining said concentration of hydrogen peroxide in said carrier gas based upon said injection rate.

15. A method as defined in claim 7, wherein said concentration of hydrogen peroxide in said carrier gas is determined based on at least two of the following methods:
   (a) providing a destroyer in said second path at a location downstream of said decontamination chamber and determining said concentration of vaporized hydrogen peroxide from a change in temperature across said destroyer;
   (b) providing a first hydrogen peroxide sensor in said decontamination chamber and determining said concentration of vaporized hydrogen peroxide based on said first hydrogen peroxide sensor;
   (c) providing a second hydrogen peroxide sensor in said plenum and determining said concentration of vaporized hydrogen peroxide based on said second hydrogen peroxide sensor;
   (d) providing a mass meter operable to measure an injection rate of said liquid hydrogen peroxide into said plenum and determining said concentration of vaporized hydrogen peroxide based on said mass; or
   (e) determining said concentration from a change in temperature of said carrier gas between a point upstream of an injection point of said liquid hydrogen peroxide into said carrier gas and a point downstream of said injection point of said liquid hydrogen peroxide.

16. A method as defined in claim 7, wherein said step (i) include the steps of:
   providing a plurality of temperature sensors at spaced-apart locations along said second path, said temperature sensors each operable to measure a temperature of said carrier gas at a location;
   providing a plurality of pressure sensors at spaced-apart locations along said second path, said pressure sensors each operable to measure a pressure of said carrier gas at a location;
   determining a dew point temperature of said vaporized hydrogen peroxide and an amount of water vapor in said carrier gas based upon readings from said plurality of temperature sensors and said plurality of pressure sensors; and
   controlling said vaporized hydrogen peroxide to a dew point temperature at or below said pre-selected temperature by controlling the following:
   (1) said volumetric flow of carrier gas moving along said second path;
   (2) a rate of introduction of said liquid hydrogen peroxide introduced into said carrier gas; and
   (3) said temperature of said carrier gas introduced into said plenum.

17. A method as defined in claim 7, wherein said step (i) includes the steps of:
   providing a hydrogen peroxide sensor operable to measure said concentration of vaporized hydrogen peroxide and a concentration of water vapor in said carrier gas along said second path;
   providing a plurality of temperature sensors at spaced-apart locations along said second path, said temperature sensors each operable to measure a temperature of said carrier gas at a location;

providing a plurality of pressure sensors at spaced-apart locations along said second path, said pressure sensors each operable to measure a pressure of said carrier gas at a location;

determining said dew point temperature of said vaporized hydrogen peroxide and said water vapor in said carrier gas based upon readings from said hydrogen peroxide sensor, said plurality of temperature sensors and said plurality of pressure sensors; and controlling said concentration of said vaporized hydrogen peroxide to a dew point temperature at or below said pre-selected temperature by controlling the following:
(1) said volumetric flow of carrier gas moving along said second path;
(2) a rate of introduction of said liquid hydrogen peroxide introduced into said carrier gas; and
(3) said temperature of said carrier gas introduced into said plenum.

18. A method of decontaminating articles, comprising the steps of:
(a) moving a plurality of articles having a predetermined temperature along a first path through a decontamination chamber;
(b) conveying a carrier gas along a second path that includes said decontamination chamber, an elongated plenum upstream from said decontamination chamber, and a destroyer disposed downstream from said decontamination chamber, said second path further comprising:
a flow sensor for sensing the volumetric flow of said carrier gas along said second path;
an injection site in said plenum for introducing an atomized mist of liquid hydrogen peroxide;
a hydrogen peroxide sensor downstream from said injection site operable to measure said concentration of vaporized hydrogen peroxide and a sensor operable to measure a concentration of water vapor in said carrier gas along said second path,
a plurality of temperature sensors at spaced-apart locations along said second path, said temperature sensors each operable to measure a temperature of said carrier gas at a location, said plurality of temperature sensors including a first temperature sensor disposed in said plenum upstream from said injection site and a second temperature sensor disposed downstream from said injection site, and
a plurality of pressure sensors at spaced-apart locations along said second path, said pressure sensors each operable to measure a pressure of said carrier gas at a location;
(c) heating said carrier gas moving along said second path to at least 105° C. at a location upstream of said plenum to a temperature sufficient to vaporize hydrogen peroxide;
(d) introducing an atomized mist of liquid hydrogen peroxide of a known concentration into said carrier gas at said injection site in said plenum to produce vaporized hydrogen peroxide in said plenum;
(e) using said hydrogen peroxide sensor, said temperature sensors and said pressure sensors to measure a temperature and a pressure of said carrier gas at discrete locations along said second path;
(f) determining the concentration of vaporized hydrogen peroxide introduced into said carrier gas based upon the temperatures of said carrier gas sensed by said first and second temperature sensors;
(g) determining a dew point temperature of said vaporized hydrogen peroxide and an amount of water vapor in said carrier gas based upon said temperature and said pressure of said carrier gas in said second path based upon a reading from said plurality of temperature sensors and said pressure sensors;
(h) introducing said vaporized hydrogen peroxide into said decontamination chamber; and
(i) controlling said concentration of said vaporized hydrogen peroxide to a dew point temperature at or below a pre-selected temperature by varying the following:
(1) said volumetric flow of carrier gas moving along said second path;
(2) a rate of introduction of said liquid hydrogen peroxide introduced into said carrier gas; and
(3) said heating of said carrier gas before said carrier gas is introduced into said plenum.

19. A method as defined in claim 18, wherein said pre-selected temperature is about 30° C. below said predetermined temperature of said articles.

20. A method of decontaminating articles, comprising the steps of:
(a) moving a plurality of articles having a predetermined temperature along a first path that includes a decontamination chamber;
(b) conveying a carrier gas along a second path that includes said decontamination chamber, an elongated plenum disposed upstream from said decontamination chamber, and a destroyer disposed downstream from said decontamination chamber, said second path further including:
a flow sensor for sensing the volumetric flow of said carrier gas along said second path,
an injection site in said plenum for introducing an atomized mist of liquid hydrogen peroxide,
a plurality of temperature sensors at spaced-apart locations along said second path, said temperature sensors each operable to measure a temperature of said carrier gas at a location, said plurality of temperature sensors including a first temperature sensor disposed in said plenum upstream from said injection site and a second temperature sensor disposed downstream from said injection site
a first hydrogen peroxide sensor in said decontamination chamber,
a second hydrogen peroxide sensor in said plenum, and
a mass meter operable to measure an injection rate of said liquid hydrogen peroxide into said plenum;
(c) heating said carrier gas moving along said second path to at least 105° C. at a location upstream of said plenum to a temperature sufficient to vaporize hydrogen peroxide;
(d) introducing an atomized mist of liquid hydrogen peroxide of a known concentration into said carrier gas in said plenum at a fixed rate to produce vaporized hydrogen peroxide in said plenum;
(e) determining the concentration of vaporized hydrogen peroxide introduced into said carrier gas based upon the temperatures of said carrier gas sensed by said first and second temperature sensors;
(f) exposing said articles in said decontamination chamber to said vaporized hydrogen peroxide; and
(g) maintaining said concentration of said vaporized hydrogen peroxide to a temperature at or below a pre-selected temperature by varying the following:

(1) said volumetric flow of carrier gas moving along said second path; and
(2) said heating of said carrier gas before said carrier gas is introduced into said plenum.

21. A method as defined in claim 20, wherein said elongated plenum is disposed above said decontamination chamber.

22. A method as defined in claim 20, wherein said preselected temperature is about 30° C. below said predetermined temperature of said articles.

23. A method as defined in claim 20, wherein said concentration of hydrogen peroxide in said carrier gas is determined based on at least one of the following methods:
   (a) determining said concentration of vaporized hydrogen peroxide from a change in temperature across said destroyer; and
   (b) determining said concentration from a change in temperature of said carrier gas between a point upstream of an injection point of said liquid hydrogen peroxide into said carrier gas and a point downstream of said injection point of said liquid hydrogen peroxide.

24. A method as defined in claim 20, wherein said step (g) includes the steps of:
   providing a hydrogen peroxide sensor operable to measure said concentration of vaporized hydrogen peroxide and a sensor operable to measure a concentration of water vapor in said carrier gas along said second path;
   providing a plurality of temperature sensors at spaced-apart locations along said second path, said temperature sensors each operable to measure a temperature of said carrier gas at a location;
   providing a plurality of pressure sensors at spaced-apart locations along said second path, said pressure sensors each operable to measure a pressure of said carrier gas at a location; and
   determining a dew point temperature of said vaporized hydrogen peroxide and said water vapor in said carrier gas based upon readings from said hydrogen peroxide sensor, said plurality of temperature sensors and said plurality of pressure sensors.

25. A method as defined in claim 20, wherein said step (g) includes the steps of:
   providing a plurality of temperature sensors at spaced-apart locations along said second path, said temperature sensors operable to measure a temperature of said carrier gas at a location;
   providing a plurality of pressure sensors at spaced-apart locations along said second path, said pressure sensors operable to measure a pressure of said carrier gas at a location; and
   determining a dew point temperature of said vaporized hydrogen peroxide and an amount of water vapor in said carrier gas based upon readings from said plurality of temperature sensors and said plurality of pressure sensors.

* * * * *